United States Patent
Wolff et al.

(10) Patent No.: US 6,936,729 B2
(45) Date of Patent: Aug. 30, 2005

(54) COMPOUND CONTAINING A LABILE DISULFIDE BOND

(75) Inventors: Jon A. Wolff, Madison, WI (US); Sean D. Monahan, Madison, WI (US); Vladimir G. Budker, Middleton, WI (US); Paul M. Slattum, Madison, WI (US); David B. Rozema, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 345 days.

(21) Appl. No.: 09/795,607

(22) Filed: Feb. 28, 2001

(65) Prior Publication Data

US 2001/0036926 A1 Nov. 1, 2001

Related U.S. Application Data

(62) Division of application No. 09/312,351, filed on May 14, 1999.
(60) Provisional application No. 60/085,764, filed on May 16, 1998.

(51) Int. Cl.[7] .......................... C11D 1/60; A61K 9/127; C12N 15/88
(52) U.S. Cl. ...................... 554/85; 435/458; 424/178.1; 424/450; 514/2; 514/17
(58) Field of Search .......................... 554/85; 435/458; 424/178.1, 450, 178.31; 514/2, 17, 71

(56) References Cited

U.S. PATENT DOCUMENTS 5,891,468 A * 4/1999 Martin et al. ................ 424/450
6,025,140 A * 2/2000 Langel et al. ................... 435/6

OTHER PUBLICATIONS

Wagner et al. Transferrin–polycation conjugates as carriers for DNA uptake into cells. Proc Natl Acad Sci U S A. May 1990;87(9):3410–4.*
MacGillivray et al. The complete amino acid sequence of human serum transferrin. Proc Natl Acad Sci U S A. Apr. 1982;79(8):2504–8.*
Voet In. Biochemistry, Second Edition, John Wiley and Sons, Pub., 1995.*
Stassen et al. Characterisation of a novel series of aprotinin–derived anticoagulants. I. In vitro and pharmacological properties. Thromb Haemost. Aug. 1995;74(2):646–54.*
Elliott et al. Effects and interactions of gentamicin, polyaspartic acid and diuretics on urine calcium concentration. J Pharmacol Exp Ther. Apr. 1995;273(1):280–4.*
Lodish et al. Cyclosporin A inhibits an initial step in folding of transferrin within the endoplasmic reticulum. J Biol Chem. Aug. 15, 1991;266(23):14835–8.*

* cited by examiner

*Primary Examiner*—David Guzo
*Assistant Examiner*—Daniel M. Sullivan
(74) *Attorney, Agent, or Firm*—Mark K. Johnson; Kirk Ekena

(57) ABSTRACT

A labile disulfide-containing compound under physiological conditions, comprising: the disulfide-containing compound having a labile disulfide bond that is either a disulfide bond that is cleaved more rapidly than oxidized glutathione or a disulfide bond constructed from thiols in which one of the constituent thiols has a lower pKa than glutathione or a disulfide bond that is activated by intramolecular attack from a free thiol.

9 Claims, No Drawings

SEQUENCE LISTING

```
<160> NUMBER OF SEQ ID NOS: 1

<210> SEQ ID NO 1
<211> LENGTH: 8
<212> TYPE: PRT
<213> ORGANISM: artificial sequence
<220> FEATURE:
<223> OTHER INFORMATION: manufactured 5,5'-dithiobis(2-nitrobenzoic
      acid) - poly-glutamic acid copolymer

<400> SEQUENCE: 1

Glu Glu Glu Glu Glu Glu Glu Glu
1               5
```

COMPOUND CONTAINING A LABILE DISULFIDE BOND

CROSS-REFERENCE TO RELATED APPLICATIONS

This specification is related to provisional application No. 60/085,764 filed on May 16, 1998 and is a divisional of Ser. No. 09/312,351 filed on May 14, 1999.

FEDERALLY SPONSORED RESEARCH

N/A

BACKGROUND

Bifunctional molecules, commonly referred to as crosslinkers, are used to connect two molecules together. Bifunctional molecules can contain homo or heterobifunctionality. The disulfide linkage (RSSR') may be used within bifunctional molecules. The reversibility of disulfide bond formation makes them useful tools for the transient attachment of two molecules. Disulfides have been used to attach a bioactive compound and another compound (Thorpe, P. E. *J. Natl. Cancer Inst.* 1987, 79, 1101). The disulfide bond is reduced thereby releasing the bioactive compound. Disulfide bonds may also be used in the formation of polymers (Kishore, K., Ganesh, K. in Advances in Polymer Science, Vol. 21, Saegusa, T. Ed., 1993).

There are many commercially available reagents for the linkage of two molecules by a disulfide bond. Additionally there are bifunctional reagents that have a disulfide bond present. Typically, these reagents are based on 3-mercaptopropionic acid, i.e. dithiobispropionate. However, the rate at which these bonds are broken under physiological conditions is slow. For example, the half life of a disulfide derived from dithiobispropionimidate, an analog of 3-mercaptopropionic acid, is 27 hours in vivo (Arpicco, S., Dos io, F., Brusa, P., Crosasso, P., Cattel, L. *Bioconjugate Chem.* 1997, 8, 327.). A stable disulfide bond is often desirable, for example when purification of linked molecules or long circulation in vivo is needed. For this reason, attempts have been made to make the disulfide less susceptible to cleavage.

It has been demonstrated that both stability, measured as reduction potential, and rate, measured as rate constants, of disulfide reduction are both related to the acidity of the thiols which constitute the disulfide. Additional factors that may affect the rate of reduction are steric interactions, and intramolecular disulfide cleavage. Looking at the difference in the rates for the reactions RSH+R'SSR'→RSSR'+R'SH and RSH+R"SSR"→RSSR"+R"SH, it has been demonstrated that log k"/k'=β(pK$_a^{R'}$–pK$_a^{R"}$), where k' and k" are the rate constant for the reactions with R'SSR' and R"SSR" respectively, pK$_a^{R'}$ and pK$_a^{R"}$ are the acidities of the thiol groups R'SH and R"SH, and β is a constant determined empirically to be 0.72. From this equation, one would predict that the reduction of a disulfide composed from relatively acidic thiols would be reduced more quickly than one composed of less acidic thiols. In support of this observation, it has been demonstrated that the disulfides cystine (pK$_a$ 8.3) and cystamine (pK$_a$ 8.2) are reduced 3–15 times faster than oxidized glutathione (pK$_a$ 8.9) (Bulaj, G., Kortemme, T., Goldenberg, D. P. *Biochemistry* 1998, 37, 8965).

It has been demonstrated that both stability (thermodynamics), measured as reduction potential (Keire D. A. *J. Org. Chem.* 1992, 57, 123), and rate (kinetics), measured as rate constants, of disulfide reduction are both related to the acidity of the thiols which constitute the disulfide (Szajewski, R. P., Whitesides, G. M. *J. Am. Chem. Soc.* 1980, 102, 2011). The increase in acidity of a thiol is dependent upon one or more of the following structural factors: the presence of electron withdrawing groups which stabilize the thiolate through sigma and pi bonds (inductive effect), the presence of electron withdrawing groups that stabilize the thiolate through space or solvent (field effects), pi bonds which allow the negative charge to be placed on other atoms (resonance stabilization), and hydrogen bond donating groups within the molecule that can interact internally with the thiolate. For example, cysteine has an amino group two atoms from the thiol, which is more electron withdrawing than the amide nitrogen that is two atoms from the thiol in glutathione. As a consequence of this difference in electron withdrawing groups, the thiol of cysteine is 0.6 pK units more acidic than glutathione, and as mentioned previously, cystine is reduced 3–15 times faster than oxidized glutathione. Another example of a relatively acidic thiol is 5-thio-2-nitrobenzoic acid, pK$_a$ 5. Its acidity is due to resonance stabilization and inductive effects. Its disulfide is rapidly reduced by all standard alkyl thiols and its colored thiolate makes it a convenient assay for thiol concentration.

SUMMARY

Described in a preferred embodiment is a process for the delivery of a compound to a cell, comprising associating a compound, containing a disulfide bond that can be cleaved under physiological conditions, with a polymer, then delivering the polymer to the cell. The polymer may comprise a first polymer and a second polymer. The first polymer and the second polymer may comprise nucleic acids, proteins, genes, antisense polymers, DNA/RNA hybrids, or synthetic polymers.

In another preferred embodiment, a biologically active compound is associated with a disulfide-containing compound, comprising: the disulfide-containing compound having a labile disulfide bond that is selected from the group consisting of (a) a disulfide bond that is cleaved more rapidly than oxidized glutathione and (b) a disulfide bond constructed from thiols in which one of the constituent thiols has a lower pKa than glutathione and (c) a disulfide bond that is activated by intramolecular attack from a free thiol.

In another preferred embodiment, a compound is provided for inserting into an organism, comprising: the compound having a disulfide bond that is labile under physiologic conditions selected from the group consisting of (a) a disulfide bond that is cleaved more rapidly than oxidized glutathione and (b) a disulfide bond constructed from thiols in which one of the constituent thiols has a lower pKa than glutathione and (c) a disulfide bond that is activated by intramolecular attack from a free thiol.

In another preferred embodiment, a process is provided for forming a compound having a labile disulfide bond for use with an organism, comprising: forming the compound having a disulfide bond selected from the group consisting of (i) a disulfide bond that is cleaved more rapidly than oxidized glutathione, and (ii) a disulfide bond constructed from thiols in which one of the constituent thiols has a lower pKa than glutathione, and (iii) a disulfide bond that is activated by intramolecular attack from a free thiol; inserting the compound into the organism.

In another preferred embodiment, a process is described for compacting a nucleic acid for delivery to a cell, comprising associating a polymer containing a disulfide bond with a nucleic acid and delivering the nucleic acid to the cell.

In another preferred embodiment, a process is described for compacting a nucleic acid for delivery to a cell comprising associating a polymer with the nucleic acid, then associating a compound containing a disulfide bond that can be cleaved under physiological conditions with the nucleic acid polymer complex, then delivering the complex to a cell.

In another preferred embodiment, a process is described for compacting a nucleic acid for delivery to a cell, comprising associating a polymer containing a disulfide bond with a nucleic acid, then associating another polymer with the disulfide containing polymer—nucleic acid complex, then delivering the complex to the cell.

In another preferred embodiment, a process is described for compacting a nucleic acid for delivery to a cell comprising associating a polymer with the nucleic acid, then associating a compound containing a disulfide bond that can be cleaved under physiological conditions with the nucleic acid polymer complex, then associating another polymer with the complex, then delivering the complex to a cell.

In another preferred embodiment, a compound is described which contains a disulfide bond that can be cleaved under physiological conditions and possesses heterobifunctional or homobifunctional groups. Such a compound can be described as a disulfide containing bifunctional molecule.

More particularly, a compound that contains an aliphatic disulfide bond with one or more electronegative (electron withdrawing groups) substituted alpha or beta to one or both of the sulfur atoms. These groups serve to lower the pKa of the constituent thiols.

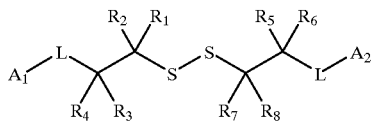

Where $R_1$, $R_2$, $R_3$, $R_4$, $R_5$, $R_6$, $R_7$, $R_8$— at least one of which is an electronegative or functionality such as OH, OR (an ether), $NH_2$, (also secondary, tertiary, and quaternary amines), $SO_3^-$, COOH, COOR (an ester), $CONH_2$, $CONR_2$ (substituted amide), a halogen (F, Cl, Br, I), $NO_2$. L is defined as a linker or spacer group that provides a connection between the disulfide and the reactive heterobifunctional or homobifunctional groups, $A_1$ and $A_2$. L may or may not be present and may be chosen from a group that includes alkanes, alkenes, alkynes, esters, ethers, glycerol, amide, urea, saccharides, polysaccharides, heteroatoms such as oxygen, sulfur, or nitrogen. The spacer may be charge positive, charge negative, charge neutral, or zwitterionic. $A_1$ and $A_2$ are reactive groups they may be identical as in a homobifunctional bifunctional molecule, or different as in a heterobifunctional bifunctional molecule. In a preferred embodiment, the disulfide compounds contain reactive groups that can undergo acylation or alkylation reactions. Such reactive groups include (but not limited to) isothiocyanate, isocyanate, acyl azide, acid halide, O-acyl urea, N hydroxysuccinimide esters, succinimide esters, amide, urea, sulfonyl chloride, aldehyde, ketone, ether, epoxide, carbonate, alkyl halide, imidoester, carboxylate, alkylphosphate, arylhalides (e.g. difluoro-dinitrobenzene) or anhydrides.

If functional group A1,A2 is an amine then A1,A2 can react with (but not restricted to) an activated carboxylic acid, isothiocyanate, isocyanate, acyl azide, alkyl halide, acid halide, N-hydroxysuccinimide ester, sulfonyl chloride, aldehyde, ketone, epoxide, carbonate, imidoester, amide, carboxylate, or alkylphosphate, arylhalides (difluoro-dinitrobenzene) or anhydrides. In other terms when function A1,A2 is an amine, then an acylating or alkylating agent can react with the amine.

If functional group A1,A2 is a sulfhydryl then A1,A2 can react with (but not restricted to) a haloacetyl derivative, activated carboxylic acid, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A1,A2 is carboxylate then A1,A2 can react with (but not restricted to) a diazoacetate, alcohol, thiol or an amine once the acid has been activated.

If functional group A1,A2 is an hydroxyl then A1,A2 can react with (but not restricted to) an activated carboxylic acid, epoxide, oxirane, or an amine in which carbonyldiimidazole is used.

If functional group A1,A2 is an aldehyde or ketone then A1,A2 can react with (but not restricted to) an hydrazine, hydrazide derivative, amine (to form a Schiff Base that may or may not be subsequently reduced by reducing agents such as $NaCNBH_3$), or a diol to form an acetal or ketal.

If functional group A1,A2 is activated carboxylic acid, isothiocyanate, isocyanate, acyl azide, N-hydroxysuccinimide ester, sulfonyl chloride, aldehyde, ketone, epoxide, carbonate, imidoester, alkylphosphate, arylhalides (difluoro-dinitrobenzene), anhydride, alkyl halide, or acid halide, p-nitrophenyl ester, o-nitrophenyl ester, pentachlorophenyl ester, pentafluorophenyl ester, carbonyl imidazole, carbonyl pyridinium, or carbonyl dimethylaminopyridinium, then A1,A2 can react with (but not restricted to) an amine, a hydroxyl, hydrazine, hydrazide, or sulfhydryl group.

If functional group A1,A2 an activated carboxylic acid, haloacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives) then A1,A2 can react with (but not restricted to) a sulfnydryl.

If functional group A1,A2 is an aldehyde, ketone, epoxide, oxirane, or an amine in which carbonyldiimidazole or N,N'-disuccinimidyl carbonate is used, then A1,A2 can react with (but not restricted to) a hydroxyl.

If functional group A1,A2 is a hydrazine, hydrazide derivative, or amine (primary or secondary) then A1,A2 can react with (but not restricted to) an aldehyde or ketone (to form a Schiff Base that may or may not be reduced by reducing agents such as $NaCNBH_3$).

Additionally, a compound which contains an aromatic disulfide bond in which the sulfur atom is bonded directly to the aromatic ring. The ring may contain 5 or more atoms.

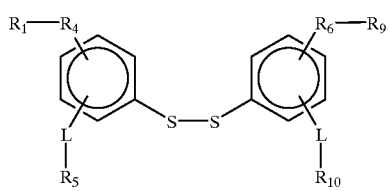

$R_1$–$R_4$, $R_6$–$R_9$—The substitution pattern on the ring may be varied to alter the reduction potential of the disulfide bond. The substiuents may be selected from the group that includes but is not limited to OH, OR (an ether), $NH_2$,(also secondary, tertiary, and quaternary amines), $SO_3^-$, COOH, COOR (an ester), $CONH_2$, $CONR_2$ (substituted amide), a halogen (F, Cl, Br, I), $NO_2$, $CH_3$ (or longer branched or straight chain, saturated, or unsaturated aliphatic group). L is defined as a linker or spacer group that provides a connection between the disulfide and the reactive heterobifunctional or homobifunctional groups. L may or may not be present and may be chosen from a group that includes alkanes, alkenes, esters, ethers, glycerol, amide, saccharides, polysaccharides, heteroatoms such as oxygen, sulfur, or nitrogen. The spacer may be charge positive, charge negative, charge neutral, or zwitterionic. $R_5$, $R_{10}$— are reactive groups they may be identical as in a homobifunctional bifunctional molecule, or different as in a heterobifunctional bifunctional molecule. In a preferred embodiment, the disulfide compounds contain reactive groups that can undergo acylation or alkylation reactions. Such reactive groups include isothiocynanate, isocynanate, acyl azide, N-hydroxysuccinimide esters, succinimide esters, sulfonyl chloride, aldehyde, epoxide, carbonate, imidoester, carboxylate, alkylphosphate, arylhalides (e.g. difluoro-dinitrobenzene) or succinic anhydride.

If functional group R5, R10 is an amine then R5, R10 can react with (but not restricted to) an activated carboxylic acid, isothiocyanate, isocyanate, acyl azide, alkyl halide, acid halide, N-hydroxysuccinimide ester, sulfonyl chloride, aldehyde, ketone, epoxide, carbonate, imidoester, amide, carboxylate, or alkylphosphate, arylhalides (difluoro-dinitrobenzene) or anhydrides. In other terms when function R5, R10 is an amine, then an acylating or alkylating agent can react with the amine.

If functional group R5, R10 is a sulfhydryl then R5, R10 can react with (but not restricted to) a haloacetyl derivative, activated carboxylic acid, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group R5, R10 is carboxylate then R5, R10 can react with (but not restricted to) a diazoacetate, alcohol, thiol or an amine once the acid has been activated.

If functional group R5, R10 is an hydroxyl then R5, R10 can react with (but not restricted to) an activated carboxylic acid, epoxide, oxirane, or an amine in which carbonyldiimidazole is used.

If functional group R5, R10 is an aldehyde or ketone then R5, R10 can react with (but not restricted to) an hydrazine, hydrazide derivative, amine (to form a Schiff Base that may or may not be subsequently reduced by reducing agents such as $NaCNBH_3$), or a diol to form an acetal or ketal.

If functional group R5, R10 is activated carboxylic acid, isothiocyanate, isocyanate, acyl azide, N-hydroxysuccinimide ester, sulfonyl chloride, aldehyde, ketone, epoxide, carbonate, imidoester, alkylphosphate, arylhalides (difluoro-dinitrobenzene), anhydride, alkyl halide, or acid halide, p-nitrophenyl ester, o-nitrophenyl ester, pentachlorophenyl ester, pentafluorophenyl ester, carbonyl imidazole, carbonyl pyridinium, or carbonyl dimethylaminopyridinium, then R5, R10 can react with (but not restricted to) an amine, a hydroxyl, hydrazine, hydrazide, or sulihydryl group.

If functional group R5, R10 an activated carboxylic acid, haloacetyl derivative, maleimide, aziridine derivative, acryloyl derivative, fluorobenzene derivatives, or disulfide derivative (such as a pyridyl disulfide or Sthio-2-nitrobenzoic acid{TNB} derivatives) then R5, R10 can react with (but not restricted to) a sulfhydryl.

If functional group R5, R10 is an aldehyde, ketone, epoxide, oxirane, or an amine in which carbonyldiimidazole or N,N'-disuccinimidyl carbonate is used, then R5, R10 can react with (but not restricted to) a hydroxyl.

If functional group R5, R10 is a hydrazine, hydrazide derivative, or amine (primary or secondary) then R5, R10 can react with (but not restricted to) an aldehyde or ketone (to form a Schiff Base that may or may not be reduced by reducing agents such as $NaCNBH_3$).

Additionally, a compound which contains a disulfide bond that is connected directly to a heterocyclic ring. The heterocyclic ring may be aromatic or aliphatic. The heterocyclic ring may contain 5 or more atoms of which 1 or more is a heteroatom (O, N, S, P), and the rest being carbon atoms

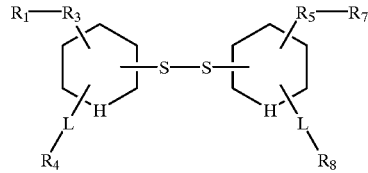

H is a heteroatom selected from the group including sulfur, oxygen, nitrogen, or phosphorus. $R_1$–$R_3$, $R_5$–$R_7$ are substituents that may be selected from the group that includes but is not limited to OH, OR (an ether), $NH_2$, (also secondary, tertiary, and quaternary amines), $SO_3^-$, COOH, COOR (an ester), $CONH_2$, $CONR_2$ (substituted amide), a halogen (F, Cl, Br, I), $NO_2$, $CH_3$ (or longer branched or straight chain, saturated, or unsaturated aliphatic group). The substitution pattern on the aromatic ring may be varied to alter the reduction potential of the disulfide bond. L is defined as a linker or spacer group that provides a connection between the disulfide and the reactive heterobifunctional or homobifunctional groups. L may or may not be present and may be chosen from a group that includes alkanes, alkenes, esters, ethers, glycerol, amide, saccharides, polysaccharides, heteroatoms such as oxygen, sulfur, or nitrogen. The spacer may be charge positive, charge negative, charge neutral, or zwitterionic. $R_4$, $R_8$ are reactive groups they may be identical as in a homobifunctional bifunctional molecule, or different as in a heterobifunctional bifunctional molecule. In a preferred embodiment, the disulfide compounds contain reactive groups that can undergo acylation or alkylation reactions. Such reactive groups include isothiocynanate, isocynanate, acyl azide, N-hydroxysuccinimide esters, succinimide esters, sulfonyl chloride, aldehyde, epoxide, carbonate, imidoester, carboxylate, alkylphosphate, arylhalides (e.g. difluoro-dinitrobenzene) or succinic anhydride.

If functional group R4, R8 is an amine then R4, R8 can react with (but not restricted to) an activated carboxylic acid, isothiocyanate, isocyanate, acyl azide, alkyl halide, acid halide, N-hydroxysuccinimide ester, sulfonyl chloride, aldehyde, ketone, epoxide, carbonate, imidoester, amide, carboxylate, or alkylphosphate, arylhalides (difluoro-dinitrobenzene) or anhydrides. In other terms when function R4, R8 is an amine, then an acylating or alkylating agent can react with the amine.

If functional group R4, R8 is a sulfhydryl then R4, R8 can react with (but not restricted to) a haloacetyl derivative, activated carboxylic acid, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group R4, R8 is carboxylate then R4, R8 can react with (but not restricted to) a diazoacetate, alcohol, thiol or an amine once the acid has been activated.

If functional group R4, R8 is an hydroxyl then R4, R8 can react with (but not restricted to) an activated carboxylic acid, epoxide, oxirane, or an amine in which carbonyldiimidazole is used.

If functional group R4, R8 is an aldehyde or ketone then R4, R8 can react with (but not restricted to) an hydrazine, hydrazide derivative, amine (to form a Schiff Base that may or may not be subsequently reduced by reducing agents such as NaCNBH$_3$), or a diol to form an acetal or ketal.

If functional group R4, R8 is activated carboxylic acid, isothiocyanate, isocyanate, acyl azide, N-hydroxysuccinimide ester, sulfonyl chloride, aldehyde, ketone, epoxide, carbonate, imidoester, alkylphosphate, arylhalides (difluoro-dinitrobenzene), anhydride, alkyl halide, or acid halide, p-nitrophenyl ester, omnitrophenyl ester, pentachlorophenyl ester, pentafluorophenyl ester, carbonyl imidazole, carbonyl pyridinium, or carbonyl dimethylaminopyridiniunr then R4, R8 can react with (but not restricted to) an amine, a hydroxyl, hydrazine, hydrazide, or sulfhlydryl group.

If functional group R4, R8 an activated carboxylic acid, haloacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives) then R4, R8 can react with (but not restricted to) a sulfhydryl.

If functional group R4, R8 is an aldehyde, ketone, epoxide, oxirane, or an amine in which carbonyldiimidazole or N,N'-disuccinimidyl carbonate is used, then R4, R8 can react with (but not restricted to) a hydroxyl.

If functional group R4, R8 is a hydrazine, hydrazide derivative, or amine (primary or secondary) then R4, R8 can react with (but not restricted to) an aldehyde or ketone (to form a Schiff Base that may or may not be reduced by reducing agents such as NaCNBH$_3$).

Additionally, a compound which contains a disulfide bond that is connected directly to a ring system(aromatic or non-aromatic) through one of the sulfur atoms and to a aliphatic carbon through the other sulfur atom. The cyclic ring may contain 5 or more atoms.

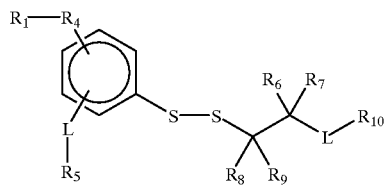

R$_1$–R$_4$ are substiuents selected from the group that includes but is not limited to H, OH, OR (an ether), NH$_2$,(also secondary, tertiary, and quaternary amines), SO$_3^-$, COOH, COOR (an ester), CONH$_2$, CONR$_2$ (substituted amide), a halogen (F, Cl, Br, I), NO$_2$, CH$_3$ (or longer branched or straight chain, saturated, or unsaturated aliphatic group). The substitution pattern on the aromatic ring may be varied to alter the reduction potential of the disulfide bond. R$_6$–R$_9$ are substiuents selected from the group that includes but is not limited to H, OH, OR (an ether), NH$_2$,(also secondary, tertiary, and quaternary amines), SO$_3^-$, COOH, COOR (an ester), CONH$_2$, CONR$_2$ (substituted amide), a halogen (F, Cl, Br, I), NO$_2$, CH$_3$ (or longer branched or straight chain, saturated, or unsaturated aliphatic group). L is defined as a linker or spacer group that provides a connection between the disulfide and the reactive heterobiflic tional or homobifunctional groups. L may or may not be present and may be chosen from a group that includes alkanes, alkenes, esters, ethers, glycerol, amide, saccharides, polysaccharides, heteroatoms such as oxygen, sulfur, or nitrogen. The spacer may be charge positive, charge negative, charge neutral, or zwitterionic. R$_5$, and R$_{10}$ are reactive groups that may be identical as in a homobifunctional bifunctional molecule, or different as in a heterobifunctional bifunctional molecule. In a preferred embodiment, the disulfide compounds contain reactive groups that can undergo acylation or alkylation reactions. Such reactive groups include isothiocynanate, isocynanate, acyl azide, N-hydroxysuccinimide esters, succinimide esters, sulfonyl chloride, aldehyde, epoxide, carbonate, imidoester, carboxylate, alkylphosphate, arylhalides (e.g. difluoro-dinitrobenzene) or succinic anhydride.

If functional group R5, R10 is an amine then R5, R10 can react with (but not restricted to) an activated carboxylic acid, isothiocyanate, isocyanate, acyl azide, alkyl halide, acid halide, N-hydroxysuccinimide ester, sulfonyl chloride, aldehyde, ketone, epoxide, carbonate, imidoester, amide, carboxylate, or alkylphosphate, arylhalides (difluoro-dinitrobenzene) or anhydrides. In other terms when function R5, R10 is an amine, then an acylating or alkylating agent can react with the amine.

If functional group R5, R10 is a sulfhydryl then R5, R10 can react with (but not restricted to) a haloacetyl derivative, activated carboxylic acid, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group R5, R10 is carboxylate then R5, R10 can react with (but not restricted to) a diazoacetate, alcohol, thiol or an amine once the acid has been activated.

If functional group R5, R10 is an hydroxyl then R5, R10 can react with (but not restricted to) an activated carboxylic acid, epoxide, oxirane, or an amine in which carbonyldiimidazole is used.

If functional group R5, R10 is an aldehyde or ketone then R5, R10 can react with (but not restricted to) an hydrazine, hydrazide derivative, amine (to form a Schiff Base that may or may not be subsequently reduced by reducing agents such as NaCNBH$_3$), or a diol to formn an acetal or ketal.

If functional group R5, R10 is activated carboxylic acid, isothiocyanate, isocyanate, acyl azide, N-hydroxysuccinimide ester, sulfonyl chloride, aldehyde, ketone, epoxide, carbonate, imidoester, alkylphosphate, arylhalides (difluoro-dinitrobenzene), anhydride, alkyl halide, or acid halide, p-nitrophenyl ester, onitrophenyl ester, pentachlorophenyl ester, pentafluorophenyl ester, carbonyl imidazole, carbonyl pyridinium, or carbonyl dimethylaminopyridinium, then R5, R10 can react with (but not restricted to) an amine, a hydroxyl, hydrazine, hydrazide, or sulfhydryl group.

If functional group R5, R10 an activated carboxylic acid, haloacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives) then R5, R10 can react with (but not restricted to) a sulfhydryl.

If functional group R5, R10 is an aldehyde, ketone, epoxide, oxirane, or an amine in which carbonyldiimidazole or N,N'-disuccinimidyl carbonate is used, then R5, R10 can react with (but not restricted to) a hydroxyl.

If functional group R5, R10 is a hydrazine, hydrazide derivative, or amine (primary or secondary) then R5, R10 can react with (but not restricted to) an aldehyde or ketone (to form a Schiff Base that may or may not be reduced by reducing agents such as NaCNBH$_3$).

Additionally, a compound which contains a disulfide bond that is connected directly to a heterocyclic ring system through one of the sulfur atoms and to a aliphatic carbon through the other sulfur atom. The heterocyclic ring may contain 5 or more atoms of which 1 or more is a heteroatom (O, N, S, P) or combinations of heteroatoms, and the rest being carbon atoms.

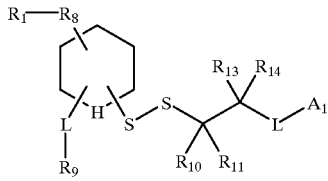

H is a heteroatom selected from the group including sulfur, oxygen, nitrogen, or phosphorus. Where $R_1$, $R_2$, $R_3$, $R_4$, $R_5$, $R_6$, $R_7$, $R_8$, $R_9$, R10, R11, $R_{12}$, R14— at least one of which is an electronegative atom or functionality such as OH, OR (an ether), $NH_2$,(also secondary, tertiary, and quaternary amines), $SO_3^-$, COOH, COOR (an ester), $CONH_2$, $CONR_2$ (substituted amide), a halogen (F, Cl, Br, I), $NO_2$. L is defined as a linker or spacer group that provides a connection between the disulfide and the reactive heterobifunctional or homobifunctional groups, $A_1$ and R9. L may or may not be present and may be chosen from a group that includes alkanes, alkenes, alkynes, esters, ethers, glycerol, amide, urea, saccharides, polysaccharides, heteroatoms such as oxygen, sulfur, or nitrogen. The spacer may be charge positive, charge negative, charge neutral, or zwitterionic. $A_1$ and R9 are reactive groups they may be identical as in a homobifunctional bifunctional molecule, or different as in a heterobifunctional bifunctional molecule. In a preferred embodiment, the disulfide compounds contain reactive groups that can undergo acylation or alkylation reactions. Such reactive groups include (but not limited to) isothiocynanate, is ocynanate, acyl azide, acid halide, O-acyl urea, N-hydroxysuccinimide esters, succinimide esters, amide, urea, sulfonyl chloride, aldehyde, ketone, ether, epoxide, carbonate, alkyl halide, imidoester, carboxylate, alkylphosphate, arythalides (e.g. difluoro-dinitrobenzene) or anhydrides.

If functional group A1,R9 is an amine then A1,R9 can react with (but not restricted to) an activated carboxylic acid, isothiocyanate, isocyanate, acyl azide, alkyl halide, acid halide, N-hydroxysuccinimide ester, sulfonyl chloride, aldehyde, ketone, epoxide, carbonate, imidoester, amide, carboxylate, or alkylphosphate, arylhalides (difluoro-dinitrobenzene) or anhydrides. In other terms when function A1,R9 is an amine, then an acylating or alkylating agent can react with the amine.

If functional group A1,R9 is a sulfhydryl then A1,R9 can react with (but not restricted to) a haloacetyl derivative, activated carboxylic acid, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A1,R9 is carboxylate then A1,R9 can react with (but not restricted to) a diazoacetate, alcohol, thiol or an amine once the acid has been activated.

If functional group A1,R9 is an hydroxyl then A1,R9 can react with (but not restricted to) an activated carboxylic acid, epoxide, oxirane, or an amine in which carbonyldiimidazole is used.

If functional group A1,R9 is an aldehyde or ketone then A1,R9 can react with (but not restricted to) an hydrazine, hydrazide derivative, amine (to form a Schiff Base that may or may not be subsequently reduced by reducing agents such as $NaCNBH_3$), or a diol to form an acetal or ketal.

If functional group A1,R9 is activated carboxylic acid, isothiocyanate, isocyanate, acyl azide, N-hydroxysuccinimide ester, sulfonyl chloride, aldehyde, ketone, epoxide, carbonate, imidoester, alkylphosphate, arylhalides (difluoro-dinitrobenzene), anhydride, alkyl halide, or acid halide, p-nitrophenyl ester, onitrophenyl ester, pentachlorophenyl ester, pentafluorophenyl ester, carbonyl imidazole, carbonyl pyridinium, or carbonyl dimethylaminopyridinium, then A1,R9 can react with (but not restricted to) an amine, a hydroxyl, hydrazine, hydrazide, or sulfhydryl group.

If functional group A1,R9 an activated carboxylic acid, haloacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives) then A1,R9 can react with (but not restricted to) a sulfbydryl.

If functional group A1,R9 is an aldehyde, ketone, epoxide, oxirane, or an amine in which carbonyldiimidazole or N,N'-disuccinimidyl carbonate is used, then A1,R9 can react with (but not restricted to) a hydroxyl.

If functional group A1,R9 is a hydrazine, hydrazide derivative, or amine (primary or secondary) then A1,R9 can react with (but not restricted to) an aldehyde or ketone (to form a Schiff Base that may or may not be reduced by reducing agents such as $NaCNBH_3$).

Additionally, a compound which contains a disulfide bond that is connected directly to a heterocyclic ring system (aromatic or non-aromatic) through one of the sulfur atoms and to an aromatic ring system through the other sulfur atom. The heterocyclic ring may contain 5 or more atoms of which 1 or more is a heteroatom (O, N, S, P) or

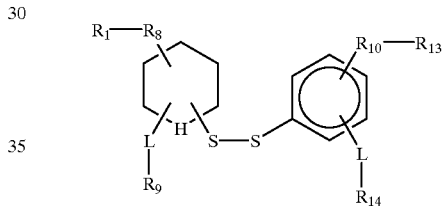

combinations of heteroatoms, and the rest being carbon atoms.

H is a heteroatom selected from the group including sulfur, oxygen, nitrogen, or phosphorus. Where $R_1$, $R_2$, $R_3$, $R_4$, $R_5$, $R_6$, $R_7$, $R_8$, $R_{10}$, $R_{11}$, $R_{12}$, $R_{13}$— at least one of which is an electronegative atom or functionality such as OH, OR (an ether), $NH_2$,(also secondary, tertiary, and quaternary amines), $SO_3^-$, COOH, COOR (an ester), $CONH_2$, $CONR_2$ (substituted amide), a halogen (F, Cl, Br, I), $NO_2$. L is defined as a linker or spacer group that provides a connection between the disulfide and the reactive heterobifunctional or homobifunctional groups, $R_9$ and $R_{14}$. L may or may not be present and may be chosen from a group that includes alkanes, alkenes, alkynes, esters, ethers, glycerol, amide, urea, saccharides, polysaccharides, heteroatoms such as oxygen, sulfir, or nitrogen. The spacer may be charge positive, charge negative, charge neutral, or zwitterionic. $R_9$ and $R_{14}$ are reactive groups they may be identical as in a homobifunctional bifunctional molecule, or different as in a heterobifunctional bifunctional molecule. In a preferred embodiment, the disulfide compounds contain reactive groups that can undergo acylation or alkylation reactions. Such reactive groups include (but not limited to) isothiocynanate, isocyanate, acyl azide, acid halide, O-acyl urea, N-hydroxysuccinimide esters, succinimide esters, amide, urea, sulfonyl chloride, aldehyde, ketone, ether, epoxide, carbonate, alkyl halide, imidoester, carboxylate, alkylphosphate, arylhalides (e.g. difluoro-dinitrobenzene) or anhydrides.

If functional group R9,R14 is an amine then R9,R14 can react with (but not restricted to) an activated carboxylic acid, isothiocyanate, isocyanate, acyl azide, alkyl halide, acid halide, N-hydroxysuccinimide ester, sulfonyl chloride, aldehyde, ketone, epoxide, carbonate, imidoester, amide, carboxylate, or alkylphosphate, arylhalides (difluoro-dinitrobenzene) or anhydrides. In other terms when function R9,R14 is an amine, then an acylating or alkylating agent can react with the amine.

If functional group R9,R14 is a sulthydryl then R9,R14 can react with (but not restricted to) a haloacetyl derivative, activated carboxylic acid, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group R9,R14 is carboxylate then R9,R14 can react with (but not restricted to) a diazoacetate, alcohol, thiol or an amine once the acid has been activated.

If functional group R9,R14 is an hydroxyl then R9,R14 can react with (but not restricted to) an activated carboxylic acid, epoxide, oxirane, or an amine in which carbonyldiimidazole is used.

If functional group R9,R14 is an aldehyde or ketone then R9,R14 can react with (but not restricted to) an hydrazine, hydrazide derivative, amine (to form a Schiff Base that may or may not be subsequently reduced by reducing agents such as $NaCNBH_3$), or a diol to form an acetal or ketal.

If functional group R9,R14 is activated carboxylic acid, isothiocyanate, isocyanate, acyl azide, N-hydroxysuccinimide ester, sulfonyl chloride, aldehyde, ketone, epoxide, carbonate, imidoester, alkylphosphate, arylhalides (difluoro-dinitrobenzene), anhydride, alkyl halide, or acid halide, p-nitrophenyl ester, o-nitrophenyl ester, pentachlorophenyl ester, pentafluorophenyl ester, carbonyl imidazole, carbonyl pyridinium, or carbonyl dimethylaminopyridinium, then R9,R14 can react with (but not restricted to) an amine, a hydroxyl, hydrazine, hydrazide, or sulfhydryl group.

If functional group R9,R14 an activated carboxylic acid, haloacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives) then R9,R14 can react with (but not restricted to) a sulfhydryl.

If functional group R9,R14 is an aldehyde, ketone, epoxide, oxirane, or an amine in which carbonyldiimidazole or N,N'-disuccinimidyl carbonate is used, then R9,R14 can react with (but not restricted to) a hydroxyl.

If functional group R9,R14 is a hydrazine, hydrazide derivative, or amine (primary or secondary) then R9,R14 can react with (but not restricted to) an aldehyde or ketone (to form a Schiff Base that may or may not be reduced by reducing agents such as $NaCNBH_3$).

DETAILED DESCRIPTION

Counterintuitive to previous efforts to synthesize bifunctional molecules with stabile disulfides, the object of the current invention is to synthesize labile disulfide molecules. In vivo, disulfides are primarily reduced by the cysteine-based thiol glutathione (γ-glutamylcystylglycine), which is present in millimolar concentrations in the cell. To increase the lability of the disulfide bond in a bifunctional molecule and its construct, we have synthesized several disulfide bond-containing bifunctional molecules that are more rapidly reduced than oxidized glutathione.

Disulfide Bond Containing Bifunctional Molecules

Bifunctional molecules, possessing either homo or heterobifunctionality (commonly referred to as crosslinkers), are used to connect two molecules together. The disulfide linkage (RSSR') may be used within bifunctional molecules. The reversibility of disulfide bond formation makes them useful tools for the transient attachment of two molecules. Physiologically, disulfides are reduced by glutathione.

A disulfide bond that is labile under physiological conditions means: the disulfide bond is cleaved more rapidly than oxidized glutathione or any disulfide constructed from thiols in which one of the constituent thiols is more acidic, lower pKa, than glutathione or is activated by intramolecular attack by a free thiol. Constituent in this case means the thiols that are bonded together in the disulfide bond. Cleavable means that a chemical bond between atoms is broken.

The present invention describes physiologically labile disulfide bond containing bifunctional molecules. The present invention is also meant to include constructs prepared from the bifunctional molecules, including polymers, peptides, proteins, nucleic acids, polymer nucleic acid complexes. Construct means any compound resulting from the chemical reaction of at least one of the reactive centers of the bifunctional molecule resulting in new chemical bond other that that resulting from hydrolysis of both reactive centers of the bifunctional molecule. Further chemical modification may occur after the formation of the construct. Crosslinking refers to the chemical attachment of two or more molecules with a bifunctional reagent. A bifunctional reagent is a molecule with two reactive ends. The reactive ends can be identical as in a homobifunctional molecule, or different as in a heterobifunctional molecule.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M. P. Stevens Polymer Chemistry: An Introduction New York Oxford University Press 1990). Template polymerization can be used to form polymers from daughter polymers.

Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields-[A-B]-Or the other approach is to have two bifunctional monomers. A-A+B-B yields-[A-A-B-B]- Generally, these reactions can involve acylation or alkylation. Acylation is defined as the introduction of an acyl group (—COR) onto a molecule. Alkylation is defined as the introduction of an alkyl group onto a molecule. If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate activated with a carbodiimide, alkylphosphate, arylhalides (difluorodinitrobenzene), anhydride, or acid halide, pnitrophenyl ester, o-nitrophenyl ester, pentachbrophenyl ester, pentafluorophenyl ester, carbonyl imidazole, carbonyl pyridinium, or carbonyl dimethylaminopyridinium. In other terms when function A is an amine then function B can be acylating or alkylating agent or amination agent.

If functional group A is a sulfhydryl then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which a carbodiimnide is used. Other additives may be utilized such as carbonyldiimidazole, dimethylamino pyridine (DMAP), N-hydroxysuccinimide or alcohol using carbodiimide and DMAP. If functional group A is an hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used. If functional group A is an aldehyde or ketone then function B can be (but not restricted to) an hydrazine, hydrazide derivative, amine (to form a Schiff Base that may or may not be reduced by reducing agents such as NaCNBH3) or hydroxyl compound to form a ketal or acetal.

Yet another approach is to have one bifunctional monomer so that A-A plus another agent yields-[A-A]-.

If function A is a sulfhydryl group then it can be converted to disulfide bonds by oxidizing agents such as iodine (I2) or NaIO4 (sodium periodate), or oxygen (O2). Function A can also be an amine that is converted to a sulfhydryl group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation. Functional group A or B in any of the above examples could also be a photoreactive group such as aryl azide (including halogenated aryl azide), diazo, benzophenone, alkyne or diazirine derivative.

Reactions of the amine, hydroxyl, sulfhydryl, carboxylate groups yield chemical bonds that are described as amide, amidine, disulfide, ethers, esters, enamine, imine, urea, isothiourea, isourea, sulfonamide, carbamate, alkylamine bond (secondary amine), carbonnitrogen single bonds in which the carbon contains a hydroxyl group, thioether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing (but not limited to) vinyl, acrylate, methacrylate, acrylamide, methacrylamide groups can undergo chain reaction which can be radical, anionic, or cationic. Chain polymerization can also be accomplished by cycle or ring opening polymerization. Several different types of free radical initiators could be used that include peroxides, hydroxy peroxides, and azo compounds such as 2,2'-Azobis(-amidinopropane) dihydrochloride (AAP).

Types of Monomers

A wide variety of monomers can be used in the polymerization processes. These include positive charged organic monomers such as amine salts, imidine, guanidine, imine, hydroxylamine, hydrozyine, heterocycle (salts) like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Monomers can also be intercalating agents such as acridine, thiazole organge, or ethidium bromide. Monomers can also contain chemical moieties that can be modified before or after the polymerization including (but not limited to) amines (primary, secondary, and tertiary), amides, carboxylic acid, ester, hydroxyl, hydrazine, alkyl halide, aldehyde, and ketone.

Other Components of the Monomers and Polymers

The polymers have other groups that increase their utility. These groups can be incorporated into monomers prior to polymer formation or attached to the polymer after its formation. These groups include: targeting groups, signals, reporter or marker molecules, spacers, steric stabilizers, chelators, polycations, polyanions, and polymers.

Targeting groups are used for targeting the polymer-nucleic acid complexes to specific cells or tissues. Examples of targeting agents include agents that target to the asialoglycoprotein receptor by using asiologlycoproteins or galactose residues. Proteins such as insulin, EGF, or transferrin can be used for targeting. Protein refers to a molecule made up of 2 or more amino acid residues connected one to another by peptide bonds between the alpha-amino group and carboxyl group of contiguous amino acid residues as in a polypeptide. The amino acids may be naturally occurring or synthetic. Peptides that include the RGD sequence can be used to target many cells. Peptide refers to a linear series of amino acid residues connected to one another by peptide bonds between the alpha-amino group and carboxyl group of contiguous amino acid residues. Polypeptide includes proteins and peptides, modified proteins and peptides, and non-natural proteins and peptides.

Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

Other targeting groups can be used to increase the delivery of the drug or nucleic acid to certain parts of the cell. For example, agents can be used to disrupt endosomes and a nuclear localizing signal (NLS) can be used to target the nucleus. A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes. The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines, acyl hydrazones, and Schiff bases.

In a preferred embodiment, a chemical reaction can be used to attach a signal to a nucleic acid complex. The signal is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced.

The signal can be a protein, peptide, lipid, steroid, sugar, carbohydrate, nucleic acid or synthetic compound. The signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin Al and the ER-retaining signal (KDEL sequence), viral components such as influenza virus hemagglutinin subunit HA-2 peptides and other types of amphipathic peptides. Cellular receptor signals are any signal that enhances the association of the gene or particle with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asialoglycoproteins or galactose residues. Other proteins such as insulin, EGF, or transferin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Reporter or marker molecules are compounds that can be easily detected. Typically they are fluorescent compounds such as fluorescein, rhodamine, Texas red, cy 5, cy 3 or dansyl compounds. They can be molecules that can be detected by UV or visible spectroscopy or by antibody interactions or by electron spin resonance. Biotin is another reporter molecule that can be detected by labeled avidin. Biotin could also be used to attach targeting groups.

A spacer is any linker known to those skilled in the art to enable one to join one moiety to another moiety. The moieties can be hydrophilic or hydrophobic. Preferred spacer groups include, but are not limited to C1–C12 alkyl, C1–C12 alkenyl, C1–C12 alkynyl, C6–C18 aralkyl, C6–C18 aralkenyl, C6–C18 aralkynyl, ester, ether, ketone, alcohol, polyol, amide, amine, polyglycol, polyamine, thiol, thio ether, thioester, phosphorous containing, and heterocyclic.

A Steric stabilizer is a long chain hydrophilic group that prevents aggregation of final polymer by sterically hindering particle to particle electrostatic interactions. Examples include: alkyl groups, PEG chains, polysaccharides, hydrogen molecules, alkyl amines. Electrostatic interactions are the non-covalent association of two or more substances due to attractive forces between positive and negative charges.

A polycation is a polymer containing a net positive charge, for example poly-L-lysine hydrobromide. The polycation can contain monomer units that are charge positive, charge neutral, or charge negative, however, the netcharge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polyc ation, polyanion, zwitterionic polymers, and neutral polymers. The term zwitterionic refers to the product (salt) of the reaction between an acidic group and a basic group that are part of the same molecule.

Salts are ionic compounds that dissociate into cations and anions when dissolved in solution. Salts increase the ionic strength of a solution, and consequently decrease interactions between nucleic acids with other cations.

A chelator is a polydentate ligand, a molecule that can occupy more than one site in the coordination sphere of an ion, particularly a metal ion, primary amine, or single proton. Examples of chelators include crown ethers, cryptates, and non-cyclic polydentate molecules. A crown ether is a cyclic polyether containing (—X-(CR1–2)n)m units, where n=1–3 and m=3–8. The X and CR1–2 moieties can be substituted, or at a different oxidation states. X can be oxygen, nitrogen, or sulfur, carbon, phosphorous or any combination thereof R can be H, C, O, S, N, P. A subset of crown ethers described as a cryptate contain a second (—X-(CR1–2)n)z strand where z=3–8. The beginning X atom of the strand is an X atom in the (—X-(CR1–2)n)m unit, and the terminal CH2 of the new strand is bonded to a second X atom in the (—X-(CR1–2)n)m unit. Non-cyclic polydentate molecules containing (—X-(CR1–2)n)m unit(s), where n=1–4 and m=1–8. The X and CR1–2 moieties can be substituted, or at a different oxidation states. X can be oxygen, nitrogen, or sulfuir, carbon, phosphorous or any combination thereof. A polychelator is a polymer associated with a plurality of chelators by an ionic or covalent bond and can include a spacer. The polymer can be cationic, anionic, zwitterionic, neutral, or contain any combination of cationic, anionic, zwitterionic, or neutral groups with a net charge being cationic, anionic or neutral, and may contain steric stabilizers, peptides, proteins, signals, or amphipathic compound for the formation of micellar, reverse micellar, or unilamellar structures. Preferably the amphipathic compound can have a hydrophilic segment that is cationic, anionic, or zwitterionic, and can contain polymerizable groups, and a hydrophobic segment that can contain a polymerizable group.

The present invention provides for the transfer of polynucleotides, and biologically active compounds into parenchymal cells within tissues in situ and in vivo, utilizing disulfide bonds that can be cleaved under physialogicval condidtions, and delivered intravasculary (U.S. patent application Ser. No. 08/571,536), intrarterially, intravenous, orally, intraduodenaly, via the jejunum (or ileum or colon), rectally, transdermally, subcutaneously, intramuscularly, intraperitoneally, intraparenterally, via direct injections into tissues such as the liver, lung, heart, muscle,spleen, pancreas, brain (including intraventricular), spinal cord, ganglion, lymph nodes, lymphatic system, adipose tissues, thryoid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands.

"Delivered" means that the polynucleotide becomes associated with the cell. The polynucleotide can be on the membrane of the cell or inside the cytoplasm, nucleus, or other organelle of the cell. The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The polynucleotides or genetic material being delivered are generally mixed with transfection reagents prior to delivery.

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, hormones, cytokines, antigens, viruses, oligonucleotides, and nucleic acids are examples of biologically active compounds. Bioactive compounds may be used interchangeably with biologically active compound for purposes of this application.

The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nuclei acid includes deoxyribonucleic acid (DNA) and ribonucleic acid (RNA). DNA may be in the form of antisense, plasmid DNA, parts of a plasmid DNA, vectors (PI, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups. "Antisense" is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothionates, and other variants of the phosphate backbone of native nucleic acids. In addition, DNA and RNA may be single, double, triple, or quadruple stranded. "Expression cassette" refers to a natural or recombinantly produced polynucleotide molecule which is capable of expressing protein(s). A DNA expression cassette typically includes a promoter (allowing transcription initiation), and a sequence encoding one or more proteins. Optionally, the expression cassette may include trancriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

The term "naked polynucleotides" indicates that the polynucleotides are not associated with a transfection reagent Cr other delivery vehicle that is required for the polynucleotide to be delivered to the cardiac muscle cell. A "transfection reagent" or "delivery vehicle" is a compound or compounds used in the prior art that bind(s) to or complex(es) with oligonucleotides or polynucleotides, and mediates their entry into cells. The transfection reagent also mediates the binding and internalization of polynucleotides into cells. Examples of transfection reagents include cationic liposomes and lipids, polyamines, calcium phosphate precipitates, histone proteins, polyethylenimine, and polylysine complexes (polyethylenimine and polylysine are both toxic). Typically, the transfection reagent has a net positive charge that binds to the polynucleotide's negative charge. The transfection reagent mediates binding of polynucleotides to cell via its positive charge (that binds to the cell membrane's negative charge) or via ligands that bind to receptors in the cell. For example, cationic liposomes or polylysine complexes have net positive charges that enable them to bind to DNA or RNA. Other delivery vehicles are also used, in the prior art, to transfer genes into cells. These include complexing the polynucleotides on particles that are then accelerated into the cell. This is termed "biolistic" or "gun" techniques.

Ionic (electrostatic) interactions are the non-covalent association of two or more substances due to attractive forces between positive and negative charges, or partial positive and partial negative charges.

Condensed Nucbic Acids: A method of condensing a polymer is defined as decreasing its linear length, also called compacting. Condensing a polymer also means decreasing the volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism. A delivered polymer can stay within the cytoplasm or nucleus apart from the endogenous genetic material. Alternatively, the polymer could recombine (become a part of) the endogenous genetic material. For example, DNA can insert into chromosomal DNA by either homologous or non-homologous recombination.

Intravascular: An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

An administration route involving the mucosal membranes is meant to include nasal, bronchial, inhalation into the lungs, or via the eyes.

Buffers are made from a weak acid or weak base and their salts. Buffer solutions resist changes in pH when additional acid or base is added to the solution. Biological, chemical, or biochemical reactions involve the formation or cleavage of ionic and/or covalent bonds. Biomolecule refers to peptides, polypeptides, proteins, enzymes, polynucleotides, oligonucleotides, viruses, antiens, carbohydrates (and conjugates), lipids, and saccharides. Enzymes are proteins evolved by the cells of living organisms for the specific function of catalyzing chemical reactions. A chemical reaction is defined as the formation or cleavage of covalent or ionic bonds. As a result of the chemical reaction a polymer can be formed. A polymer is defined as a compound containing more than two monomers. A monomer is a compound that can be attached to itself or another monomer and thus a form a polymer.

Transdermal refers to application to mammal skin in which drug delivery occurs by crossing the dermal layer.

Hydrocarbon means containing carbon and hydrogen atoms; and halohydrocarbon means containing carbon, halogen (F, Cl, Br, I), and hydrogen atoms.

Alkyl means containing $sp^3$ hybridized carbon atoms; alkenyl means containing two or more $sp^2$ hybridized carbon atoms; aklkynyl means containing two or more sp hybridized carbon atoms; aralkyl means containing one or more aromatic ring(s) in addition containing $sp^3$ hybridized carbon atoms; aralkenyl means containing one or more aromatic ring(s) in addition to containing two or more $sp^2$ hybridized carbon atoms; aralkynyl means containing one or more aromatic ring(s) in addition to containing two or more sp hybridized carbon atoms; steroid includes natural and unnatural steroids and steroid derivatives.

A steroid derivative means a sterol, a sterol in which the hydroxyl moity has been modified (for example, acylated), or a steroid hormone, or an analog thereof.

Carbohydrates include natural and unnatural sugars (for example glucose), and sugar derivatives (a sugar derivative means a system in which one or more of the hydroxyl groups on the sugar moiety has been modified (for example acylated), or a system in which one or more of the hydroxyl groups is not present).

Polyoxyethylene means a polymer having two to six (n=2–3000) ethylene oxide units ($-(CH_2CH_2O)_n-$) or a derivative thereof.

R is meant to be any compatible group, for example hydrogen, alkyl, alkenyl, alkynyl, aralkyl, aralkenyl, or aralkynyl, and can include heteroatoms (N, O, S), and carbonyl groups.

A compound is a material made up of two or more elements.

Electron withdrawing group is any chemical group or atom composed of electronegative atom(s), that is atoms that tend to attract electrons. Resonance stabilization is the ability to distribute charge on multiple atoms through pi bonds. The inductive effective, in a molecule, is a shift of electron density due to the polarization of a bond by a nearby electronegative or electropositive atom.

Steric hindrance, or sterics, is the prevention or retardation of a chemical reaction because of neighboring groups on the same molecule.

An activated carboxylate is a carboxylic acid derivative that reacts with nucleophiles to form a new covalent bond. Nucleophiles include nitrogen, oxygen and sulfur-containing compounds to produce ureas, amides, carbonates, esters, and thioesters. The carboxylic acid may be activated by various agents including carbodiimides, carbonates, phosphoniums, uroniums to produce activated carboxylates acyl ureas, acylphosphonates, and carbonates. Activation of carboxylic acid may be used in conjunction with hydroxy and amine-containing compounds to produce activated carboxylates N-hydroxysuccinimide esters, hydroxybenzotriazole esters, N-hydroxy-5-norbornene-endo-2,3-dicarboximide esters, p-nitrophenyl esters, pentafluorophenyl esters, 4-dimethylaminopyridinium amides, and acyl imidazoles.

A nucleophile is a species possessing one or more electronrich sites, such as an unshared pair of electrons, the negative end of a polar bond, or pi electrons.

EXAMPLES

Example 1

Synthesis of 5,5'-Dithiobis(2-nitrobenzoate) propionitrile 5,5'-dithiobis(2-nitrobenzoic acid) (500 mg, 1.26 mmol, Aldrich Chemical Company) was taken up in 4.0 mL dioxane. Dicylohexylcarbodiimide (540 mg, 2.6 mmol, Aldrich Chemical Company) and 3-hydroxypropionitrile (240 µL, 188 mg, 2.60 mmol, Aldrich Chemical Company) were added. The reaction mixture was stirred overnight at room temperature. The precipitate was removed by centrifugation, and the solvent concentrated under reduced pressure. The residue was washed with saturated sodium bicarbonate, water, and brine; and dried over magnesium sulfate. Solvent removal (aspirator) yielded 696 mg yellow/orange foam. The residue was purified using normal phase HPLC (Alltech econosil, 250×22 nm), flow rate=9.0 mL/min, mobile phase=1% ethanol in chloroform, retention time=13 min. Removal of solvent (aspirator) afforded 233 mg (36.8%) of 5,5'-dithiobis(2-nitrobenzoate)propionitrile as a yellow oil. TLC (silica: 5% methanol in chloroform; Rf=0.51). $H^1$ NMR 8.05 (d, 4 H), 7.75 (m, 4H), 4.55 (t, 4H), 2.85 (t, 4H).

Example 2

Synthesis of Dimethyl 5,5'-dithiobis(2-nitrobenzoate)propionimidate-2 HCl 5,5'-Dithiobis(2-nitrobenzoate)propionitrile (113 mg, 0.226 mmol) was taken up in 500. µL anhydrous chloroform. Anhydrous methanol (20.0 µL, 0.494 mmol, Aldrich Chemical Company) was added. The resulting solution was cooled to 0° C. on an ice bath, and HCl gas was bubbled through the solution for a period of 10 minutes. The resulting solution was placed in a −20° C. freezer for a period of 48 hours. During this time a yellow oil formed. The oil was washed thoroughly with chloroform and dried under vacuum to afford 137 mg (95.8%) of dimethyl 5,5'-dithiobis(2-nitrobenzoate)propionimidate-2 HCl as a yellow foam.

Example 3

Polymerization of N-(2-Aminoethyl)-1,3-propanediamine and Dimethyl 5,5'-dithiobis(2-nitrobenzoate)propionimidate-2 HCl on a DNA Template.

Procedure:

Template polymerization was carried out in 25 mM HEPES buffer, pH 8.0.

N-(2-Aminoethyl)-1,3-propanediamine (48 µg, 0.3 mM, Aldrich Chemical Company) was added to a 0.5 mL solution of pCIluc DNA (25 mg, .075 mM in phosphate, 2.6 µg/µL pCIluc; prepared according to Danko, I., Williams, P., Herweijer, H. et al. Hum. Mol. Genetics (1997) in press). Dimethyl 5,5'-dithiobis(2-nitrobenzoate)propionimidate-2 HCl (500 µg, 0.78 mM) was added, and the solution was vortexed. The reaction was incubated at room temperature for one hour. A fine yellow precipitate was observed to form during the incubation period. The reaction was centrifuged to remove the precipitate. A portion of the reaction (10 µL) was reduced with 10 mM dithiothreitol (10 µL) to break the disulfide bonds forming the polymer. Portions (0.5 µg) of the intact polymer and the reduced polymer were analyzed on a 1% agarose gel.

Example 4

Formation of DNA/Poly-L-Lysine/Dimethyl 5,5'-Dithiobis(2-nitrobenzoate) propionimidate-2 HCl Complexes pDNA/Poly-L-lysine hydrobromide complexes were prepared by combining plasmid DNA (25 µg) with Poly-L-lysine hydrobromide (95 µg, MW 35 kDa, Aldrich Chemical Company) in 0.5 mL 25 mM Hepes buffer pH 8.0, and the solution was vortexed to mix. The resulting solution was divided into 3 portions. One portion was incubated at room temperature for 2 hrs. To the second portion was added dimethyl 5,5'-dithiobis(2-nitrobenzoate)propionimidate-2 HCl (472 mg, 1.5 mmol), the solution was mixed, and incubated at room temperature for 2 hrs. To the third sample was added dimethyl 3,3'-dithiobispropionimidate (1.1 mg, 1.5 mmol), the solution was mixed, and incubated at room temperature for 2 hrs. After 2 hrs. the samples were then centrifuged at 12000 rpm for five minutes.

Ninety degree light scattering measurements were performed (Shimadzo RF-1501 Fluorescence Spectrophotometer). The wavelength setting was 700 nm for both the incident beam and detetion of scattering light. The slits for both beams were fixed at 10 nm. The particle size of the resulting complex was determined by light scattering (Brookhaven ZetaPlus Particle Sizer). After determining the initial intensity of scattered light, 15 µL 5 M NaCl solution was added to the complexes while the intensity of scattered light was monitored.

The addition of salt to the non-caged particles led to an immediate increase in the turbidity of the solution indicating aggregation. The non caged sample also became visibly cloudy. The addition of salt to the particles caged using dimethyl 3,3'-dithiobispropionimidate led to an increase in turbidity of approximately 33%. The addition of salt to the dimethyl 5,5'-dithiobis(2-nitrobenzoate)propionimidate-2 HCl caged complexes lead to no visible rise in turbidity. The particle size of the dimethyl 5,5'-dithiobis(2-nitrobenzoate) propionimidate-2 HCl caged particles was determined (Brookhaven Zeta Plus Particle Sizer) in 150 mM NaCl (physiological concentration). The mean particle diameter was found to be 89.7 nm, 67% of the total number of particles were under 100 nm in size.

The example indicates that dimethyl 5,5'-dithiobis(2-nitrobenzoate)propionimidate-2 HCl caged DNA. The particles formed are stable in physiological salt, and are under 100 nm in size.

Example 5

Demonstration of Reducibility of Disulfide Bond in vitro pDNA (pCI Luc)/polyethyleneimine (25 kDa, Aldrich Chemical Company)/dimethyl 3,3'-dithiobispropionimidate and pDNA/polyethyleneimine/dimethyl 5,5'-dithiobis(2-nitrobenzoate)propionimidate-2 HCl complexes were prepared in 25 mM HEPES buffer pH 8.0. All complexes were prepared at pDNA/polyethyleneimine ratios of 1/3. Dimethyl 3,3'-dithiobispropionimidate and dimethyl 5,5'-dithiobis(2-nitrobenzoate) propionimidate-2 HCl were added at the following ratios: 0,3,6,12, and 25. Complexes were incubated 0.5 hour at room temperature, and centrifuged 5 minutes at 12,000 rpm prior to transfection. Transfections were carried out in 35 mm wells. At the time of transfection, HepG2 monolayers, at approximately 50% confluency, were washed once with PBS (phosphate buffered saline), and subsequently stored in serum-free media (Opti-MEM, Gibco BRL). The complexes were diluted in Opti-MEM and added by drops, 5.0 µg DNA/well, to the cells. After a 4 hour incubation period at 37° C., the media containing the complexes was aspirated from the cells, and replaced with complete growth media, DMEM with 10% fetal bovine serum (Sigma). After an additional incubation of 42 hours, the cells were harvested and the lysate was assayed for luciferase expression (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used.

pDNA/polyethyleneimine/dimethyl 3,3'-dithiobispropionimidate and pDNA/polyethyleneimine/dimethyl 5,5'-dithiobis(2-nitrobenzoate)propionimidate-2 HCl particles were transfected into Hep G2 cells. pDNA/polyethyleneimine complexes were also transfected as a control. The cell lysates were then analyzed for the expression of luciferin. The results show that while the dimethyl 3,3'-dithiobispropionimidate complexes gave expression results below baseline (<200 RLU), the dimethyl 5,5'-dithiobis(2-nitrobenzoate)propionimidate-2 HCl/pDNA/polyethyleneimine complexes gave levels of expression that were as high as 120,000 RLU.

The physiologically labile disulfide bonds preserlt in the dimethyl 5,5'-dithiobis(2-nitrobenzoate)propionimidate-2 HCl complexes can be reduced by cultured cells, while the disulfide bonds present in the dimethyl 3,3'-dithiobispropionimidate complexes cannot.

Example 6

Synthesis of 5,5'-dithiobis[(3"-bromopropyl)-2-nitrobenzoate]

5,5'-dithiobis-(2-nitrobenzoic acid) (500 mg, 1.26 mmol, Aldrich Chemical Company) and 3-bromopropanol (368 mg, 2.65 mmol, Aldrich Chemical Company) were taken up in 7.0 mL THF. Dicyclohexylcarbodiimide (545 mg, 2.65 mmol, Aldrich Chemical Company) was added, and the reaction mixture was stirred overnight at ambient temperature. The precipitate was removed by filtration, and the solution was concentrated under reduced pressure to afford 430 mg (54%) of 5,5'-dithiobis[(3"-bromopropyl)-2-nitrobenzoate] as a yellow oil.

Example 7

Synthesis of 5,5'-dithiobis[(3"-ammonio-{N,N-dimethy>N-propionitrile}propyl bromide)2-nitrobenzoate]

5,5'-dithiobis[(3"-bromopropyl)-2-nitrobenzoate] was taken up in 2.0 mL THF, and 3-dimethylaminopropionitrile (193 mg, 1.96 mmol, Aldrich Chemical Company) was added. After 3 days at ambient temperature, the salt was precipitated from solution with $Et_2O$, and purified by reverse phase HPLC (C-18 Aquasil 200×20 mm) using a gradient from 20 to 80% methanol over 20 minutes (elution at 15 minutes). The solvent was removed under reduced pressure to afford 15.2 mg (3%) 5,5'-dithiobis[(3"-ammonio-{N,N-dimethyl-N-propionitrile}propyl bromide)2-nitrobenzoate]. $H^1$-NMR ($CD_3OD$) 8.4–8.6 (m, 6H), 5.0 (t, 4 H), 4.35 (t, 4H), 4.1 (m, 4H), 2.85 (m, 4H), 3.75 (m, 16H).

Synthesis of Dimethyl 5,5'-dithiobis[(3"-ammonio-(N,N-dimethy-N-propioimidate)propyl chloride) 2-nitrobenzoate]-hydrochloride

Example 8

Synthesis of 5,5'-dithiobis[(3"-ammonio-(N,N-dimethyl-N-propioimidate)propyl chloride) 2-nitrobenzoate]

5,5'-dithiobis[(3"-ammonio-{N,N-dimethyl-N-propionitrile}propyl bromide)2-nitrobenzoate] (15.2 mg, 0.018 mmol) was taken up in 1 mL of methanol. The solution was saturated with HCl at 0° C. The resulting solution was held at −20° C. for 1 week. $Et_2O$ was added and the precipitate collected by filtration to afford 8.3 mg (47%) of dimethyl 5,5'-dithiobis[(3"-ammonio-(N,N-dimethyl-N-propioimidate)propyl chloride) 2-nitrobenzoate]-hydrochloride.

Example 9

Synthesis of N,N'-Bis(t-BOC)-L-cystine

To a solution of L-cystine (1 gm,4.2 mmol, Aldrich Chemical Company) in acetone (10 mL) and water (10 mL) was added 2-(tert-butoxycarbonyloxyimino)-2-phenylacetonitrile (2.5 gm,10 mmol, Aldrich Chemical Company) and triethylamine (1.4 mL, 10 mmol, Aldrich Chemical Company). The reaction was allowed to stir overnight at room temperature. The water and acetone was then by rotary evaporation resulting in a yellow solid. The diBOC compound was then isolated by flash chromatography on silica gel eluting with ethyl acetate 0.1% acetic acid.

Example 10

Synthesis of L-cystine -1,4-bis(3-aminopropyl) piperazine Copolymer

To a solution of N,N'-Bis(t-BOC)-L-cystine (85 mg, 0.15 mmol) in ethyl acetate (20 mL) was added N,N'-dicyclohexylcarbodiimide (108 mg, 0.5 mmol) and N-hydroxysuccinimide (60 mg, 0.5 mmol). After 2 hr, the solution was filtered through a cotton plug and 1,4-bis(3-aminopropyl)piperazine (54 μL, 0.25 mmol) was added. The reaction was allowed to stir at room temperature for 16 h. The ethyl acetate was then removed by rotary evaporation and the resulting solid was dissolved in trifluoroacetic acid (9.5 mL), water (0.5 mL) and triisopropylsilane (0.5 mL). After 2 h, the trifluoroacetic acid was removed by rotary evaporation and the aqueous solution was dialyzed in a 15,000 MW cutoff tubing against water (2×2l) for 24 h. The solution was then removed from dialysis tubing, filtered through 5 μM nylon syringe filter and then dried by lyophilization to yield 30 mg of polymer.

Example 11

Synthesis of Guanidino-L-cystine

To a solution of cystine (1 gm, 4.2 mmol) in ammonium hydroxide (10 mL) in a screw-capped vial was added O-methylisourea hydrogen sulfate (1.8 gm, 10 mmol). The vial was sealed and heated to 60° C. for 16 h. The solution was then cooled and the ammonium hydroxide was removed by rotary evaporation. The solid was then dissolved in water (20 mL), filtered through a cotton plug. The product was then isolated by ion exchange chromatography using Bio-Rex 70 resin and eluting with hydrochloric acid (100 mM).

Example 12

Synthesis of Guanidino-L-cystine 1,4-bis(3-aminopropyl)piperazine Copolymer

To a solution of guanidino-L-cystine (64 mg, 0.2 mmol) in water (10 mL) was slowly added N,N'-dicyclohexylcarbodiimide (82 mg, 0.4 mmol) and N-hyroxysuccinimide (46 mg, 0.4 mmol) in dioxane (5 mL). After 16 hr, the solution was filtered through a cotton plug and 1,4-bis(3-aminopropyl)piperazine (40 μL, 0.2 mmol) was added. The reaction was allowed to stir at room temperature for 16 h and then the aqueous solution was dialyzed in a 15,000 MW cutoff tubing against water (2×2 l) for 24 h. The solution was then removed from dialysis tubing, filtered through 5 μM nylon syringe filter and then dried by lyophilization to yield 5 mg of polymer.

Example 13

The particle size of pDNA-L-cystine-1,4-bis(3-aminopropyl)piperazine copolymer and DNA-guanidino-L-cystine1, 4-bis(3-aminopropyl) piperazine Copolymer Complexes.

To a solution of pDNA (10 μg/mL) in 0.5 mL 25 mM HEPES buffer pH 7.5 was added 10 μg/mL L-cystine-1,4-bis(3-aminopropyl)piperazine copolymer or guanidino-L, cystine-1,4-bis(3-aminopropyl)piperazine copolymer. The size of the complexes between DNA and the polymers were measured. For both polymers, the size of the particles were approximately 60 nm.

Example 14

Condensation of DNA with L-cystine—1,4-bis(3-aminopropyl)piperazine copolymer and decondensation of DNA upon Addition of glutathione Fluorescein labeled DNA was used for the determination of DNA condensation in complexes with L-cystine-1,4-bis (3-aminopropyl)piperazine copolymer. pDNA was modified to a level of 1 fluorescein per 100 bases using Mirus' LabelIt™ Fluorescein kit. The fluorescence was determined using a fluorescence spectrophotometer (Shimadzu RF-1501 spectrofluorometer) at an excitation wavelength of 495 nm and an emission wavelength of 530 nm. (Trubetskoy, V. S., Slattum, P. M., Hagstrom, J. E., Wolff, J. A., Budker, V. G., "Quantitative Assessment of DNA Condensation," Anal. Biochem (1999) incorporated by reference).

The intensity of the fluorescence of the fluorescein-labeled DNA (10 μg/mL) in 0.5 mL of 25 mM HEPES buffer pH 7.5 was 300 units. Upon addition of 10 μg/mL of L-cystine-1,4-bis(3-aminopropyl)piperazine copolymer, the intensity decreased to 100 units. To this DNA-polycation sample was added 1 mM glutathione and the intensity of the fluorescence was measured. An increase in intensity was measured to the level observed for the DNA sample alone. The half life of this increase in fluorescence was 8 minutes.

The experiment indicates that DNA complexes with physiologically-labile disulfide-containing polymers are cleavable in the presence of the biological reductant glutathione.

Example 15

Mouse Tail Vein Injection of DNA-L-cystine-1,4-bis(3-aminopropyl)piperazine copolymer and DNA-guanidino-L-cystine1, 4-bis(3-aminopropyl) piperazine copolymer complexes Plasmid delivery in the tail vein of ICR mice was performed as described. To PCILuc DNA (50 μg) in 2.5 mL H$_2$O was added either L-cystine-1,4-bis(3-aminopropyl) piperazine copolymer, guanidino-L-cystine-1,4-bis(3-aminopropyl)piperazine copolymer, or poly-L-lysine (34,000 MW, Sigma Chemical Company) (50 μg). The samples were then injected into the tail vein of mice using a 30 gauge, 0.5 inch needle. One day after injection, the animal was sacrificed, and a luciferase assay was conducted.

| Polycation | ng/liver |
|---|---|
| poly-L-lysine | 6.2 |
| L-cystine-1,4-bis(3-aminopropyl)piperazine copolymer | 439 |
| guanidino-L-cystine1,4-bis(3-aminopropyl)piperazine copolymer | 487 |

The experiment indicates that DNA complexes with the physiologically-labile disulfide-containing polymers are capable of being broken, thereby allowing the luciferase gene to be expressed.

Example 16

Rat Intramuscle Injection of DNA-L-cystine—1,4-bis(3-aminopropyl)piperazine copolymer and DNA-guanidino-L-cystine1, 4-bis(3-aminopropyl) piperazine copolymer complexes.

Plasmid delivery intro rat leg was performed as described (Wolff, J. A., Malone, R. W., Williams, P., Chong, W., Acsadi, G., Jani, A. and Felgner, P. L. Direct gene transfer into mouse muscle in vivo. Science, 1465–1468, 1990.). To pCILuc DNA (100 μg/mL, 2.5 mL) was added L-cystine-1,4-bis(3-aminopropyl)piperazine copolymer or guanidino-L-cystine-1,4-bis(3-aminopropyl)piperazine copolymer (100 μg/mL) and then injected into the leg muscles of a rat. After 7 days, the animal was sacrificed and a luciferase assay was conducted.

| DNA complex | amount luciferase (ng) per leg |
|---|---|
| no polycation | 3.3 |
| L-cystine-1,4-bis(3-aminopropyl)piperazine copolymer | 4.5 |
| guanidino-L-cystine1,4-bis(3-aminopropyl)piperazine copolymer | 6.5 |

The experiment indicates that DNA complexes with the physiologically-labile disulfide-containing polymers are capable of being broken, thereby allowing the luciferase gene to be expressed.

Example 17

Injection of DNA-L-cystine-1,4-bis(3-aminopropyl) piperazine copolymer complex and pDNA (pCI Luc)/5,5'-Dithiobis(2-nitrobenzoic acid)-1,4-Bis(3-aminopropyl)piperazine copolymer complex and pDNA (pCI Luc)/5,5'-dithiobis(2-nitrobenzoic acid)-1,4-bis(3-aminopropyl)piperazine-Folate copolymer Complexes into the intestinal lumen of mice Intestinal cells were transfected by injecting pDNA solutions into the mesenteric vasculature. A 3-cm section of the small intestines was clamped, blocking both vascular inflow and outflow. A volume of 250 μl containing 50 μg pCILuc and 50 μg poly(ethylenimine) (Aldrich Chemical Co. MW 25,000 MW), L-cystine-1,4-bis(3-aminopropyl)piperazine copolymer, pDNA (pCI Luc)/5,5'-dithiobis(2-nitrobenzoic acid)-1,4-bis(3-aminopropyl)piperazine copolymer, and pDNA (pCI Luc)/5,5'-dithiobis(2-nitrobenzoic acid)-1,4-bis (3-aminopropyl)piperazine-folate copolymer complexes were injected into the intestinal lumen of mice. After 3 minutes, the clamps were removed. One day after DNA delivery, the mice were sacrificed, the injected section of the intestines was excised, cut in 3 cm sections and assayed for luciferase expression. Different areas of the intestines were targeted (duodenum, jejunum, ileum).

| Complex | Amount luciferase (pg) | | |
|---|---|---|---|
| | Duodenum | jejunum | ileum |
| DNA-poly(ethylenimine) | 0.5 | 3.0 | 1.7 |
| DNA-L-cystine-1,4-bis(3-aminopropyl)piperazine copolymer | 6.2 | 3.7 | 2.8 |
| pDNA (pCI Luc)/5,5'-dithiobis(2-nitrobenzoic acid)-1,4-bis(3-aminopropyl)piperazine copolymer | 42 | 20 | 226 |
| pDNA (pCI Luc)/5,5'-dithiobis(2-nitrobenzoic acid)-1,4-bis(3-aminopropyl)piperazine-folate copolymer | 36 | 1.9 | 51 |

The experiment indicates that DNA complexes with labile disulfide-containing polymers are capable of being broken, thereby allowing the luciferase gene to be expressed.

Example 18

Synthesis of 5,5'-Dithiobis[succinimidyl(2-nitrobenzoate)]

5,5'-dithiobis(2-nitrobenzoic acid) (50.0 mg, 0.126 mmol, Aldrich Chemical Company) and N-hyroxysuccinimide (29.0 mg, 0.252 mmol, Aldrich Chemical Company) were taken up in 1.0 mL dichloromethane. Dicylohexylcarbodi-imide (52.0 mg, 0.252 mmol) was added and the reaction mixture was stirred overnight at room temperature. After 16 hr, the reaction mixture was partitioned in EtOAc/$H_2O$. The organic layer was washed 2x$H_2O$, 1xbrine, dried (MgSO$_4$) and concentrated under reduced pressure. The residue was taken up in $CH_2Cl_2$, filtered, and purified by flash column chromatography on silica gel (130x30 mm, EtOAc:$CH_2Cl_2$ 1:9 eluent) to afford 42 mg (56%) 5,5'-dithiobis[succinimidyl(2-nitrobenzoate)] as a white solid.

$H^1$ NMR (DMSO) 7.81–7.77 (d, 2H), 7.57–7.26 (m, 4H), 3.69 (s, 8 H).

Example 19

Synthesis of 5,5'-Dithiobis(2-nitrobenzoic acid)-1,4-Bis(3-aminopropyl)piperazine Copolymer 1,4-Bis(3-aminopropyl)piperazine (10 μL, 0.050 mmol, Aldrich Chemical Company) was taken up in 1.0 mL methanol and HCl (2 mL, 1 M in Et$_2$O, Aldrich Chemical Company) was added. Et$_2$O was added and the resulting HCl salt was collected by filtration. The salt was taken up in 1 mL DMF and 5,5'-dithiobis[succinimidyl(2-nitrobenzoate)] (30 mg, 0.050 mmol) was added. The resulting solution was heated to 80 C and diisopropylethylamine (35 μL, 0.20 mmol, Aldrich Chemical Company) was added by drops. After 16 hr, the solution was cooled, diluted with 3 mL $H_2O$, and dialyzed in 12,000–14,000 MW cutoff tubing against water (2x2 L) for 24 h. The solution was then removed from dialysis tubing and dried by lyophilization to yield 23 mg (82%) of 5,5'-dithiobis(2-nitrobenzoic acid)-1,4-bis(3-aminopropyl)piperazine copolymer.

Example 20

Particle Sizing of pDNA (pCI Luc)/5,5'-Dithiobis(2-nitrobenzoic acid)-1,4-Bis(3-aminopropyl)piperazine Copolymer Complexes To 50 μg pDNA in 3 mL Ringers (0.85% sodium chloride, 0.03% potassium chloride, 0.03% calcium chloride) was added 170 μg 5,5'-Dithiobis(2-nitrobenzoic acid)-1,4-Bis(3-aminopropyl)piperazine Copolymer. Particle sizing (Brookhaven Instruments Coporation, ZetaPlus Particle Sizer, 190, 532 nm) indicated an effective diameter of 92 nm for the complex. A 50 μg pDNA in 3 mL Ringers sample indicated no particle formation.

5,5'-Dithiobis(2-nitrobenzoic acid)-1,4-Bis(3-aminopropyl)piperazine Copolymer condenses pDNA, forming small particles.

Example 21

Mouse Tail Vein Injections of pDNA (pCI Luc)/5,5'-Dithiobis(2-nitrobenzoic acid)-1,4-Bis(3-aminopropyl)piperazine Copolymer Complexes Four complexes were prepared as follows:

Complex I: pDNA (pCI Luc, 200 μg) in 1 mL $H_2O$ and diluted with 9 mL Ringers prior to injection.

Complex II: pDNA (pCI Luc, 200 μg) was mixed with poly-L-lysine (378 μg, MW 3400, Sigma Chemical Company) in 1 mL $H_2O$ and diluted with 9 mL Ringers prior to injection.

Complex III: pDNA (pCI Luc, 200 μg) was mixed with 5,5'-Dithiobis(2-nitrobenzoic acid)-1,4-Bis(3-aminopropyl)piperazine Copolymer (400 μg) in 1 mL $H_2O$ and diluted with 9 mL Ringers prior to injection.

Complex IV: pDNA (pCI Luc, 200 μg) was mixed with Histone HI (1.2 mg, Sigma Chemical Company) in 1 mL $H_2O$ and diluted with 9 mL Ringers prior to injection.

2.5 mL and 250 μL tail vein injections of the complex were performed (Zhang, G., Budker, V., Wolff, J, *High Levels of Foreign Gene Expression in Hepatocytes from Tail Vein Injections of Naked Plasmid DNA. Human Gene Therapy*, July, 1999, incorporated by reference). Results reported are for liver expression. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used.

Results from 2.5 mL injections

Complex I: 1,976,000

Complex II: 128,000

Complex III: 5,025,000

Complex IV: 1,960

Results from 250 µL injections

Complex I: 985

Complex III: 1,140

Results indicate an increased level of luciferase expression in pDNA/5,5'-Dithiobis(2-nitrobenzoic acid)-1,4-Bis(3-aminopropyl)piperazine Copolymer complexes over pCI Luc DNA itself, pCI Luc DNA/poly-L-lysine complexes, and pCI Luc DNA/Histone Hi complexes. These results also indicate that the pDNA is being released from the pDNA/5,5'-Dithiobis(2-nitrobenzoic acid)-1,4-Bis(3-aminopropyl)piperazine Copolymer complexes, and is accessible for transcription. 250 µL injection results were similar for both pDNA/5,5'-Dithiobis(2-nitrobenzoic acid)-1,4-Bis(3-aminopropyl)piperazine Copolymer complexes and pCI Luc DNA.

Example 22

Synthesis of 5,5'-Dithiobis(2-nitrobenzoic acid)-1,4-Bis(3-aminopropyl)piperazine-Tris(2-aminoethyl)amine Copolymer 1,4-Bis(3-aminopropyl)piperazine (2.4 µL, 0.012 mmol, Aldrich Chemical Company) and tris(2-aminoethyl)amine (0.51 µL, 0.0034 mmol, Aldrich Chemical Company) were taken up in 0.5 mL methanol and HCl (1 mL, 1 M in $Et_2O$, Aldrich Chemical Company) was added $Et_2O$ was added and the resulting HCl salt was collected by filtration. 5,5'-dithiobis[succinimidyl (2-nitrobenzoate)] (10 mg, 0.016 mmol) was added and the mixture was taken up in 0.4 mL DMSO and 0.4 mL THF. The resulting solution was stirred at room temperature and diisopropylethylamine (5.9 µL, 0.042 mmol, Aldrich Chemical Company) was added by drops. After 16 hr, the solution was diluted with 3 mL $H_2O$, and dialyzed in 12,000–14,000 MW cutoff tubing against water (2×2 L) for 48 h. The solution was then removed from dialysis tubing and dried by lyophilization to yield 2.7 mg (30%) of 5,5'-dithiobis(2-nitrobenzoic acid)-1,4-bis(3-aminopropyl)piperazine-tris(2-aminoethyl)amine copolymer.

Example 23

Synthesis of 5,5'-Dithiobis(2-nitrobenzoic acid)-Tetraethylenepentamine Copolymer Tetraethylenepentamine (3.2 µL, 0.017 mmol, Aldrich Chemical Company) was taken up in 1.0 mL dichloromethane and HCl (1 mL, 1 M in $Et_2O$, Aldrich Chemical Company) was added $Et_2O$ was added and the resulting HCl salt was collected by filtration. The salt was taken up in 1 mL DMF and 5,5'-dithiobis[succinimidyl (2-nitrobenzoate)] (10 mg, 0.017 mmol) was added. The resulting solution was heated to 80° C. and diisopropylethylamine (15 µL, 0.085 mmol, Aldrich Chemical Company) was added by drops. After 16 hr, the solution was cooled, diluted with 3 mL $H_2O$, and dialyzed in 12,000–14,000 MW cutoff tubing against water (2×2 L) for 24 h.

The solution was then removed from dialysis tubing and dried by lyophilization to yield 5.8 mg (62%) of 5,5'-dithiobis(2-nitrobenzoic acid)-tetraethylenepentamine copolymer.

Example 24

Mouse Tail Vein Injections of pDNA (pCI Luc)/5,5'-Dithiobis(2-nitrobenzoic acid)-Tetraethylenepentamine Copolymer Complexes Complexes were prepared as follows:

Complex I: pDNA (pCI Luc, 200 µg) was added to 300 µL DMSO then 2.5 mL Ringers was added.

Complex II: pDNA (pCI Luc, 200 µg) was added to 300µL DMSO then 5,5'-Dithiobis(2-nitrobenzoic acid)-Tetraethylenepentamine Copolymer (336 µg) was added followed by 2.5 mL Ringers.

2.5 mL tail vain injections of the complex were performed as previously described. Results reported are for liver expression, and are the average of two mice. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, BadWildbad, Germany) luminometer was used.

250 µL injections

Complex I: 25,200,000

Complex II: 21,000,000

Results indicate that pDNA (pCI Luc)/5,5'-Dithiobis(2-nitrobenzoic acid)-tetraethylenepentamine copolymer complexes are nearly equivalent to pCI Luc DNA itself in 2.5 mL injections. This indicates that the pDNA is being released from the complex and is accessible for transcription.

Example 25

Synthesis of 5,5'-Dithiobis(2-nitrobenzoic acid)-Tetraethylenepentamine-Tris(2-aminoethyl)amine Copolymer Tetraethylenepentamine (2.3 µL, 0.012 mmol, Aldrich Chemical Company) and tris(2-aminoethyl)amine (0.51 µL, 0.0034 mmol, Aldrich Chemical Company) were taken up in 0.5 mL methanol and HCl (1 mL, 1 M in $Et_2O$, Aldrich Chemical Company) was added. $Et_2O$ was added and the resulting HCl salt was collected by filtration. The salt was taken up in 1 mL DMF and 5,5'-dithiobis[succinimidyl (2-nitrobenzoate)] (10 mg, 0.017 mmol) was added. The resulting solution was heated to 80° C. and diisopropylethylamine (15 µL, 0.085 mmol, Aldrich Chemical Company) was added by drops. After 16 hr, the solution was cooled, diluted with 3 mL $H_2O$, and dialyzed in 12,000–14,000 MW cutoff tubing against water (2×2 L) for 24 h. The solution was then removed from dialysis tubing and dried by lyophilization to yield 6.9 mg (77%) of 5,5'-dithiobis(2-nitrobenzoic acid)-tetraethylenepentamine-tris(2-aminoethyl)amine copolymer.

Example 25

Mouse Tail Vein Injections of pDNA (pCI Luc)/5,5'-Dithiobis(2-nitrobenzoic acid)-Tetraethylenepentamine-Tris(2-aminoethyl)amine Copolymer Complexes Complexes were prepared as follows:

Complex I: pDNA (pCI Luc, 200 µg) was added to 300 µL DMSO then 2.5 mL Ringers was added.

Complex II: pDNA (pCI Luc, 200 μg) was added to 300μL DMSO then 5,5'-Dithiobis(2-nitrobenzoic acid)-Tetraethylenepentamine-Tris(2-aminoethyl)amine Copolymer (324 μg) was added followed by 2.5 mL Ringers.

2.5 mL tail vain injections of the complex were preformed as previously described. Results reported are for liver expression, and are the average of two mice. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468,1990.). A Lumat LB 9507 (EG&G Berthold, BadWildbad, Germany) luminometer was used.

250 μL injections

Complex I: 25,200,000

Complex II: 37,200,000 pDNA (pCI Luc)/5,5'-Dithiobis(2-nitrobenzoic acid)-tetraethylenepentamine-Tris(2-aminoethyl)amine Copolymer Complexes are more effective than pCI Luc DNA in 2.5 mL injections. Indicating that the pDNA is released from the complex and is accessible for transcription.

Example 26

Synthesis of 5,5'-Dithiobis(2-nitrobenzoic acid)-N,N'-Bis(2-aminoethyl)-1,3-propanediamine Copolymer N,N'-Bis(2-aminoethyl)-1,3-propanediamine (2.8 μL, 0.017 mmol, Aldrich Chemical Company) was taken up in 1.0 mL dichoromethane and HCl (1 mL, 1 M in $Et_2O$, Aldrich Chemical Company) was added. $Et_2O$ was added and the resulting HCl salt was collected by filtration. The salt was taken up in 1 mL DMF and 5,5'-dithiobis[succinimidyl(2-nitrobenzoate)] (10 mg, 0.017 mmol) was added. The resulting solution was heated to 80° C. and diisopropylethylamine (12 μL, 0.068 mmol, Aldrich Chemical Company) was added by drops. After 16 hr, the solution was cooled, diluted with 3 mL $H_2O$, and dialyzed in 12,000–14,000 MW cutoff tubing against water (2×2 L) for 24 hr. The solution was then removed from dialysis tubing and dried by lyophilization to yield 5.9 mg (66%) of 5,5'-dithiobis(2-nitrobenzoic acid)-N,N'-bis(2-aminoethyl)-1,3-propanediamine Copolymer.

Example 27

Mouse Tail Vein Injections of pDNA (pCI Luc)/5,5'-Dithiobis(2-nitrobenzoic acid)-N,N'-Bis(2-aminoethyl)-1,3-propanediamine Copolymer Complexes Complexes were prepared as follows:

Complex I: pDNA (pCI Luc, 200 μg) was added to 300 μL DMSO then 2.5 mL Ringers was added Complex II: pDNA (pCI Luc, 200 μg) was added to 300 μL DMSO then 5,5'-Dithiobis(2-nitrobenzoic acid)-N,N'-Bis(2-aminoethyl)-1,3-propanediamine Copolymer (474 [g) was added followed by 2.5 mL Ringers.

Tail vain injections of 2.5 mL of the complex were preformed as previously described. Results reported are for liver expression, and are the average of two mice. Luciferase expression was determined as previously reported.

Results: 2.5 mL injections

Complex I: 25,200,000

Complex II: 341,000 pDNA (pCI Luc)/5,5'-Dithiobis(2-nitrobenzoic acid)-tetraethylenepentamine Copolymer Complexes provides luciferase expression indicating that the pDNA is being released from the complex and is accessible for transcription.

Example 28

Synthesis of 5,5'-Dithiobis(2-nitrobenzoic acid)-N,N'-Bis(2-aminoethyl)-1,3-propanediamine-Tris(2-aminoethyl)amine Copolymer N,N'-Bis(2-aminoethyl)-1,3-propanediamine (2.0 μL, 0.012 mmol, Aldrich Chemical Company) and tris(2-aminoethyl)amine (0.51 μL, 0.0034 mmol, Aldrich Chemical Company) were taken up in 0.5 mL methanol and HCl (1 mL, 1 M in $Et_2O$, Aldrich Chemical Company) was added. $Et_2O$ was added and the resulting HCl salt was collected by filtration. The salt was taken up in 1 mL DMF and 5,5'-dithiobis[succinimidyl(2-nitrobenzoate)] (10 mg, 0.017 mmol) was added. The resulting solution was heated to 80° C. and diisopropylethylamine (12 μL, 0.068 mmol, Aldrich Chemical Company) was added by drops. After 16 hr, the solution was cooled, diluted with 3 mL $H_2O$, and dialyzed in 12,000–14,000 MW cutoff tubing against water (2×2 L) for 24 hr. The solution was then removed from dialysis tubing and dried by lyophilization to yield 6.0 mg (70%) of 5,5'-dithiobis(2-nitrobenzoic acid)-N,N'-bis(2-aminoethyl)-1,3-propanediamine-tris(2-aminoethyl)amine copolymer.

Example 29

Mouse Tail Vein Injections of pDNA (pCI Luc)/5,5'-Dithiobis(2-nitrobenzoic acid)-N,N'-Bis(2-aminoethyl)-1,3-propanediamine-Tris(2-aminoethyl)amine Copolymer Complexes Complexes were prepared as follows:

Complex I: pDNA (pCI Luc, 200 μg) was added to 300 μL DMSO then 2.5 mL Ringers was added.

Complex IT: pDNA pCI Luc, 200 μg) was added to 300μL DMSO then 5,5'-Dithiobis(2-nitrobenzoic acid)-N,N'-Bis(2-aminoethyl)-1,3-propanediamine-Tris(2-aminoethyl)amine Copolymer (474 μg) was added followed by 2.5 mL Ringers.

Tail vain injections of 2.5 mL of the complex were preformed as previously described. Results reported are for liver expression, and are the average of two mice. Luciferase expression was determined as previously reported.

Results: 2.5 mL injections

Complex I: 25,200,000

Complex II: 1,440,000

Results indicate that pDNA (pCI Luc)/5,5'-Dithiobis(2-nitrobenzoic acid)-N,N'-Bis(2-aminoethyl)-1,3-propanediamine-Tris(2-aminoethyl)amine Copolymer Complexes are less effective than pCI Luc DNA in 2.5 mL injections. Although the complex was less effective, the luciferase expression indicates that the pDNA is being released from the complex and is accessible for transcription.

Example 30

Intramuscular Injections of Complexes from pDNA (pCI Luc)/Physiologically Labile Disulfide Bond Containing Polymers on Mouse Seven complexes were prepared as follows:

Complex I: pDNA (pCI Luc, 40 μg) was added to 586 μL glucose (290 mM)-HEPES (5 mM, pH 8).

Complex II: pDNA (pCI Luc, 40 μg) was added to 577 μL glucose (290 mM)-HEPES (5 mM, pH 8). To this solution was added 5,5'-Dithiobis(2nitrobenzoic acid)-1,4-Bis(3-aminopropyl)piperazine Copolymer (9 μL, 200 μg).

Complex III: pDNA (pCI Luc, 40 μg) was added to 573 μL glucose (290 mM)-HEPES (5 mM, pH 8). To this solution was added 5,5'-Dithiobis(2-nitrobenzoic acid)-1,4-Bis(3-aminopropyl)piperazine Copolymer (13 μL, 200 μg).

Complex IV: pDNA (pCI Luc, 40 μg) was added to 574 μL glucose (290 mM)-HEPES (5 mM, pH 8). To this solution was added 5,5'-Dithiobis(2-nitrobenzoic acid)-Tetraethylenepentamine Copolymer (12 μL, 70 μg).

Complex V: pDNA (pCI Luc, 40 μg) was added to 576 μL glucose (290 mM)-HEPES (5 mM, pH 8). To this solution was added 5,5'-Dithiobis(2-nitrobenzoic acid)-Tetraethylenepentamine-Tris(2-aminoethyl)amine Copolymer (10 μL, 65 μg).

Complex VI: pDNA (pCI Luc, 40 μg) was added to 581 μL glucose (290 mM)-HEPES (5 mM, pH 8). To this solution was added 5,5'-Dithiobis(2-nitrobenzoic acid)-N,N'-Bis(2-aminoethyl)-1,3-propanediamine Copolymer (5 μL, 94 μg).

Complex VII: pDNA (pCI Luc, 40 μg) was added to 570 μL glucose (290 mM)-HEPES (5 mM, pH 8). To this solution was added 5,5'-Dithiobis(2-nitrobenzoic acid)-N,N'-Bis(2-aminoethyl)-1,3-propanediamine-Tris(2-aminoethyl)amine Copolymer (16 μL, 94 μg).

Direct muscle injections of 150 μL of the complex were preformed as previously described (See Budker, V., Zhang, G., Danko, I., Williams, P., and Wolff, J., "The Efficient Expression Of Intravascularly Delivered DNA In Rat Muscle," Gene Therapy 5, 272–6(1998); Wolff, J. A., Malone, R. W., Williams, P., Chong, W., Acsadi, G., Jani, A. and Felgner, P. L. Direct gene transfer into mouse muscle in vivo. Science, 1465–1468, 1990, which are incorporated herein by reference.). Seven days post injection, the animals were sacrificed, and the muscle harvested. Samples were homogenized in lux buffer (1 mL), and centrifuged for 15 minutes at 4000 RPM. Luciferase expression was determined as previously reported. Results reported for left quadracep:right quadracep (Complex IV-only injected into left quadracep).

Results:

Complex I: RLU=1,900:4,316

Complex II: RLU=13,433:20,640

Complex III: RLU=10,156:39,491

Complex IV: RLU=9,888:

Complex V: RLU=19,565:5,806

Complex VI: RLU=270:427

Complex VII: RLU=973:6,000

The complexes prepared from pCI Luc DNA/ Physiologically Labile Disulfide Bond Containing Polymers are effective in direct muscle injections. The luciferase expression indicates that the pDNA is being released from the complex and is accessible for transcription. Complexes prepared with 5,5'-Dithiobis(2-nitrobenzoic acid)-1,4-Bis(3-aminopropyl)piperazine Copolymer were the most effective, giving luciferase expression levels 2 to 10 times as high as pDNA.

Example 31

Synthesis of 5,5'-Dithiobis(2-nitrobenzoic acid)-Pentaethylenehexamine Copolymer Pentaethylenehexamine (4.2 μL, 0.017 mmol, Aldrich Chemical Company) was taken up in 1.0 mL dichloromethane and HCl (1 mL, 1 M in Et$_2$O, Aldrich Chemical Company) was added Et$_2$O was added and the resulting HCl salt was collected by filtration. The salt was taken up in 1 mL DMF and 5,5'-dithiobis[succinimidyl(2-nitrobenzoate)] (10 mg, 0.017 mmol) was added. The resulting solution was heated to 80° C. and diisopropylethylamine (12 μL, 0.068 mmol, Aldrich Chemical Company) was added by drops. After 16 hr, the solution was cooled, diluted with 3 mL H$_2$O, and dialyzed in 12,000–14,000 MW cutoff tubing against water (2×2 L) for 24 hr. The solution was then removed from dialysis tubing and dried by lyophilization to yield 5.9 mg (58%) of 5,5'-dithiobis(2-nitrobenzoic acid)-pentaethylenehexamine Copolymer.

Example 32

Synthesis of 5,5'-Dithiobis(2-nitrobenzoic acid)-Pentaethylenehexamine-Tris(2-aminoethyl)amine Copolymer Pentaethylenehexamine (2.9 μL, 0.012 mmol, Aldrich Chemical Company) and tris(2-arninoethyl)amine (0.51 μL, 0.0034 mmol, Aldrich Chemical Company) were taken up in 0.5 InL methanol and HCl (1 mL, 1 M in Et$_2$O, Aldrich Chemical Company) was added. Et$_2$O was added and the resulting HCl salt was collected by filtration. The salt was taken up in 1 mL DMF and 5,5'-dithiobis[succinimidyl(2-nitrobenzoate)] (10 mg, 0.017 mmol) was added. The resulting solution was heated to 80° C. and disopropylethylamine (12 μL, 0.068 mmol, Aldrich Chemical Company) was added by drops. After 16 hr, the solution was cooled, diluted with 3 mL H$_2$O, and dialyzed in 12,000–14,000 MW cutoff tubing against water (2×2 L) for 24 h. The solution was then removed from dialysis tubing and dried by lyophilization to yield 6.0 mg (64%) of 5,5'-dithiobis(2-nitrobenzoic acid)-pentaethylenehexamine-tris(2-aminoethyl)amine copolymer.

Example 33

Synthesis of 5,5'-Dithiobis(2-nitrobenzoic acid)-N-(3-Aminopropyl)-1,3-propanediamine Copolymer 5,5'-Dithiobis[succinimidyl(2-nitrobenzoate)] (2.5 mg, 0.0042 mmol) was taken up in 10 μL of DMF. N-(3-aminopropyl)-1,3-propanediamine (0.6 μL, 0.004 mmol, Aldrich Chemical Company) was added with 10 μL HEPES 250 mM, pH 7.5. After 1 hr the solution was concentrated under reduced pressure. The resulting residue was dissolved in 0.42 mL DMSO. Analysis of the solution on SDS-PAGE versus poly-L-lysisne hydrobromide (MW of 1000, 7500, 15000) indicated an approximate molecular weight range of 3500–8000 for the polymer.

Example 34

Synthesis of 5,5'-dithiobis(2-nitrobenzoic acid)-1, 4bis(3-aminopropyl)piperazine-Folate Copolymer Folate-PEG(3400 MW)-NH2 was prepared according to the known procedure (Lee, R. J., Low, P. S. Biochimica et Biophysica Acta 1233, 1995, 134–144). Folate-PEG-NH2 was acylated with succinylated N-(3-(BOC)aminopropyl)-1,3-propaneamine(BOC)amine. Removal of the BOC protecting groups afforded the Folate monomer.

1,4-bis(3-aminopropyl)piperazine (5.0 µL, 0.023 mmol, Aldrich Chemical Company) and folate monomer (5.0 mg, 0.0012 mmol) were taken up in 0.4 mL methanol and HCl (1 mL, 1 M in Et$_2$O, Aldrich Chemical Company) was added. The resulting suspension was concentrated under reduced pressure to afford a white solid. The salt was taken up in 0.5 mL DMF and 5,5'-dithiobis[succinimidyl(2-nitrobenzoate)] (14 mg, 0.025 mmol) was added. The resulting solution was heated to 80° C. and diisopropylethylamine (18 µL, 0.10 ramol, Aldrich Chemical Company) was added by drops. After 16 hr, the solution was cooled, diluted with 3 mL H$_2$O, and dialyzed in 12,000–14,000 MW cutoff tubing against water (2×2 L) for 24 h. The solution was then removed from dialysis tubing and dried by lyophilization to yield 13 mg (68%) of 5,5'-dithiobis(2-nitrobenzoic acid)-1, 4-bis(3-aminopropyl) piperazine-folate copolymer.

Example 35

Synthesis of 5,5'-Dithiobis(2-nitrobenzoic acid)-Poly-Glutamicacid (8mer) Copolymer (SEQ. ID NO. 1)

H$_2$N-EEEEEEEE-NHCH$_2$CH$_2$NH$_2$ (5.0 mg, 0.0052 mmol, Genosis) was taken up in 0.1 mL HEPES (250 mM, pH 7.5). 5,5'-dithiobis[succinimidyl(2-nitrobenzoate)] (3.1 mg, 0.0052) was added with 0.2 mL DMSO and the mixture was stirred overnight at room temperature. After 16 hr the solution was heated to 70° C. for 10 min, cooled to room temperature and diluted to 1.10 mL with DMSO.

Example 36

Complex Formation with 5,5'-Dithiobis(2-nitrobenzoic acid)-Poly-Glutamicacid (8mer) Copolymer Fluorescein labeled DNA was used for the determination of DNA condensation in complexes with 5,5'-Dithiobis(2-nitrobenzoic acid)-Poly-Glutamicacid (8mer) Copolymer. pDNA was modified to a level of 1 fluorescein per 20 bases using Mirus' LabelIT™ Fluorescein kit. The fluorescence was determined using a fluorescence spectrophotometer (Shimadzo RF-1501 Fluorescence Spectrophotometer), at an excitation wavelength of 497 nm, and an emission wavelength of 520 nm.

---

---

We claim:

1. A complex for delivering a nucleic acid to a mammalian cell comprising:
   said nucleic acid reversibly compacted by a polymer, said polymer comprising a plurality of labile disulfide bonded monomers, to form said complex wherein said polymer contains labile disulfide monomers containing disulfide bonds constructed from thiols in which at least one of the constituent thiols has a lower thiol pKa than glutathione thiol pKa when measured under the same conditions.

2. The complex of claim 1 wherein the polymer is selected from the group consisting of a polycation, a polyanion, a neutral polymer and an amphipathic polymer.

3. The complex of claim 1 wherein the polymer contains a ligand.

4. A physiologically labile polymer for condensing nucleic acid comprising:
   a plurality of monomers linked via labile disulfide bonds that are cleavable by reduced glutathione more rapidly than the disulfide bond of oxidized glutathione when measured under the same conditions, wherein said polymer condenses said nucleic acid more strongly than said monomers.

5. The polymer of claim 4 wherein said labile disulfide bonds are constructed from thiols in which at least one of the constituent thiols has a lower thiol pKa than glutathione thiol pKa when measured under the same conditions.

6. The polymer of claim 4 wherein the polymer is selected from the group consisting of a polycation, a polyanion, a neutral polymer, and an amphipathic polymer.

7. The polymer of claim 4 wherein the polymer contains a ligand.

8. The polymer of claim 4 wherein said labile disulfide bonds are cleaved by intramolecular attack from a free thiol.

9. The complex of claim 1 wherein said complex is less than 100 nm in size.

* * * * *